US011702394B2

(12) United States Patent
Gouw et al.

(10) Patent No.: US 11,702,394 B2
(45) Date of Patent: Jul. 18, 2023

(54) INHIBITORS OF PHOSPHOLIPID SYNTHESIS AND METHODS OF USE

(71) Applicant: The Board of Trustees of the Leland Stanford Junior University, Stanford, CA (US)

(72) Inventors: Arvin Gouw, San Francisco, CA (US); Dean W. Felsher, San Mateo, CA (US); Feng Jin, Stanford, CA (US); Richard N. Zare, Stanford, CA (US); Katherine Margulis, San Francisco, CA (US); Steven R. Schow, Redwood City, CA (US); Robert J. Greenhouse, Newark, CA (US); David Loughhead, Belmont, CA (US); Steven Richards, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 93 days.

(21) Appl. No.: 16/968,836

(22) PCT Filed: Feb. 22, 2019

(86) PCT No.: PCT/US2019/019185

§ 371 (c)(1),
(2) Date: Aug. 10, 2020

(87) PCT Pub. No.: WO2019/165232

PCT Pub. Date: Aug. 29, 2019

(65) Prior Publication Data

US 2021/0002240 A1 Jan. 7, 2021

Related U.S. Application Data

(60) Provisional application No. 62/634,526, filed on Feb. 23, 2018.

(51) Int. Cl.
*A61P 35/00* (2006.01)
*C07D 295/092* (2006.01)
*C07C 311/08* (2006.01)

(52) U.S. Cl.
CPC .......... *C07D 295/092* (2013.01); *A61P 35/00* (2018.01); *C07C 311/08* (2013.01)

(58) Field of Classification Search
CPC ........................................................ A61P 35/00
See application file for complete search history.

(56) References Cited

U.S. PATENT DOCUMENTS

| | | | |
|---|---|---|---|
| 8,927,553 B2 | 1/2015 | Dhanoa | |
| 2012/0083471 A1 | 4/2012 | Townsend et al. | |
| 2012/0184600 A1 | 7/2012 | Liu et al. | |

OTHER PUBLICATIONS

American Chemical Society. Chemical Abstract Service. RN 1158383-11-9. First made available to public/entered into STN: Jun. 16, 2009. (Year: 2009).*

Wydysh et al. 'Design and Synthesis of Small Molecule Glycerol 3-Phosphate Acyltransferase Inhibitors', J, Med. Chem. 2009, vol. 52, pp. 3317-3327.

* cited by examiner

*Primary Examiner* — John S Kenyon

(74) *Attorney, Agent, or Firm* — Pamela J. Sherwood; Bozicevic, Field & Francis LLP

(57) ABSTRACT

Inhibitors of Glycerol 3-Phosphate Acyltransferase (GPAT) are provided; and methods of use in the treatment of cancer; and treatment of conditions relating to metabolic syndrome and hyperlipidemia.

16 Claims, 13 Drawing Sheets

GFZ1.1

GFZ1.2

GFZ1.5

GFZ2

C
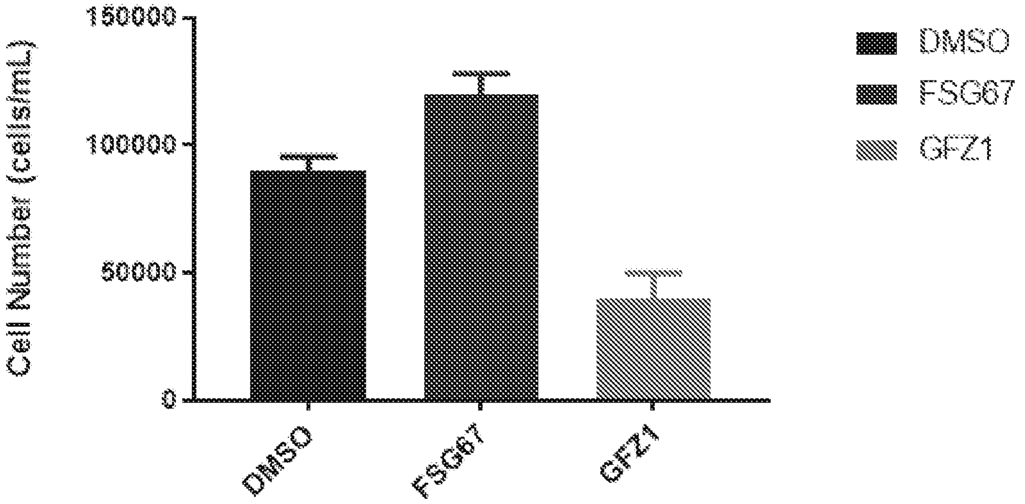
D
GFZ1
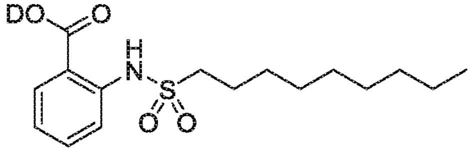
FIGURE 12, continued

INHIBITORS OF PHOSPHOLIPID SYNTHESIS AND METHODS OF USE

CROSS-REFERENCE

This application claims the benefit of U.S. Provisional Patent Application No. 62/634,526, filed Feb. 23, 2018, which application is incorporated herein by reference in its entirety.

GOVERNMENT RIGHTS

This invention was made with Government support under contract RO1 CA184384 awarded by the National Institutes of Health. The Government has certain rights in this invention.

BACKGROUND

Synthesis of mammalian phospholipids is based on a diacylglycerol unit that is contributed by either diacylglycerol or CDP-diacylglycerol. These phospholipid precursors are generated from phosphatidic acid. First, 1-acylglycerol-3-phosphate (also called lyso-phosphatidic acid or LPA) is made from glycerol-3-phosphate via glycerol-3-phosphate acyltransferase or from the acylation of dihydroxyacetone phosphate and reduction of 1-acyl-dihydroxyacetone phosphate to 1-acylglycerol-3-P. Membranes of the ER and mitochondria contain distinct isoforms of glycerol-3-phosphate acyltransferase (GPAT). The 1-acylglycerol-3-phosphate is then converted into phosphatidic acid by acyltransferase activities. Subsequently, diacylglycerol is generated from phosphatidic acid by the action of phosphatidic acid phosphatase-1. Alternatively, CDP-diacylglycerol synthase, an enzyme that is associated primarily with the ER catalyzes a reaction between CTP and phosphatidic acid leading to formation of CDP-diacylglycerol.

Phospholipids are involved in stabilizing proteins within the membrane, facilitating the active conformational structure of proteins, and as cofactors in enzymatic reactions. Phospholipids are essential for the absorption, transport and storage of lipids. Phospholipids are secreted into the bile to aid in the digestion and absorption of dietary fat. They form the monolayer on the surface of lipoproteins which function to transport neutral lipids throughout the body. Finally, phospholipids serve as a reservoir for signaling molecules, such as arachidonic acid, phosphatidate, diacylglycerol and inositol trisphosphate.

Targeted control of phospholipid synthesis through enzyme-specific inhibition is of interest for a variety of therapeutic purposes. The present disclosure provides compositions and methods for this purpose.

SUMMARY

Provided are pharmacologic inhibitors of glycerol-3-phosphate acyltransferase (GPAT) and methods of use thereof. In some embodiments an effective dose of the GPAT inhibitor is administered to an individual for the treatment of cancer. In some embodiments the cancer is MYC-driven. In some embodiments the cancer is screened and determined to be lipogenesis-dependent. In other embodiments an effective dose of the GPAT inhibitor is administered to an individual for treatment of metabolic syndrome and related disorders, including without limitation hyperlipidemia, diabetes, fatty liver disease, obesity, etc.

In some embodiments, the GPAT inhibitor is of any of formulae (IA) to (II):

(IA)

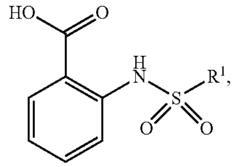

(IB)

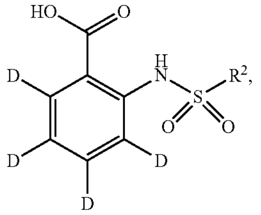

(IC)

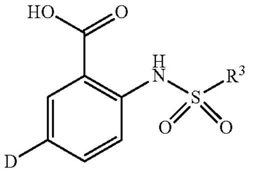

or (II)

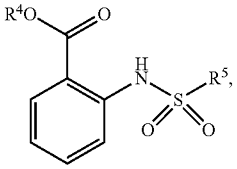

wherein:

$R^1$ is selected from deuterated alkyl and substituted deuterated alkyl;

$R^2$, $R^3$ and $R^5$ are each independently selected from alkyl, substituted alkyl, deuterated alkyl and substituted deuterated alkyl;

$R^4$ is selected from alkyl, substituted alkyl, alkenyl, alkynyl, cycloalkyl, cycloalkyl(alkyl), heterocycloalkyl, heterocycloalkyl(alkyl), aryl, substituted aryl, aryl(alkyl), substituted aryl(alkyl), halo(alkyl), heteroaryl, heteroaryl(alkyl);

or a pharmaceutically acceptable salt or solvate thereof.

In some embodiments a pharmaceutical formulation is provided, comprising a GPAT inhibitor of any of formulae (IA)-(II), and a pharmaceutically acceptable excipient. In some embodiments the formulation is provided in a unit dose form. In some embodiments the formulation is provided in sterile packaging for clinical use.

In some embodiments the use is provided of a GPAT inhibitor in the manufacture of a medicament for the treatment of cancer, or of metabolic syndrome and related disorders.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 12A In mouse derived MYC-induced HCC EC4 line, there is no difference in cell viability 48 hours after treatment with FSG67 (1-100 μM dose) or GFZ1 (1-100 μM dose). Statistical significance by t-test for MYC ON compared to control, *P<0.05, P<0.01, *P<0.001. FIG. 12B In mouse-derived MYC-induced RCC E28 line, there is no difference in cell viability 48 hours after treatment with FSG67 (1-100 μM dose) or GFZ1 (1-100 μM dose). Statistical significance by t-test for MYC ON compared to control, *P<0.05, P<0.01, *P<0.001. FIG. 12C In human MYC-induced Burkitt's Lymphoma line P493, there is significant difference in cell viability 48 hours after treatment with FSG67 (1-100 μM dose) or GFZ1 (1-100 μM dose). Statistical significance by t-test for MYC ON compared to control, *P<0.05, P<0.01, *P<0.001. FIG. 12D Structure of GFZ1.

DEFINITIONS

Figure 1:
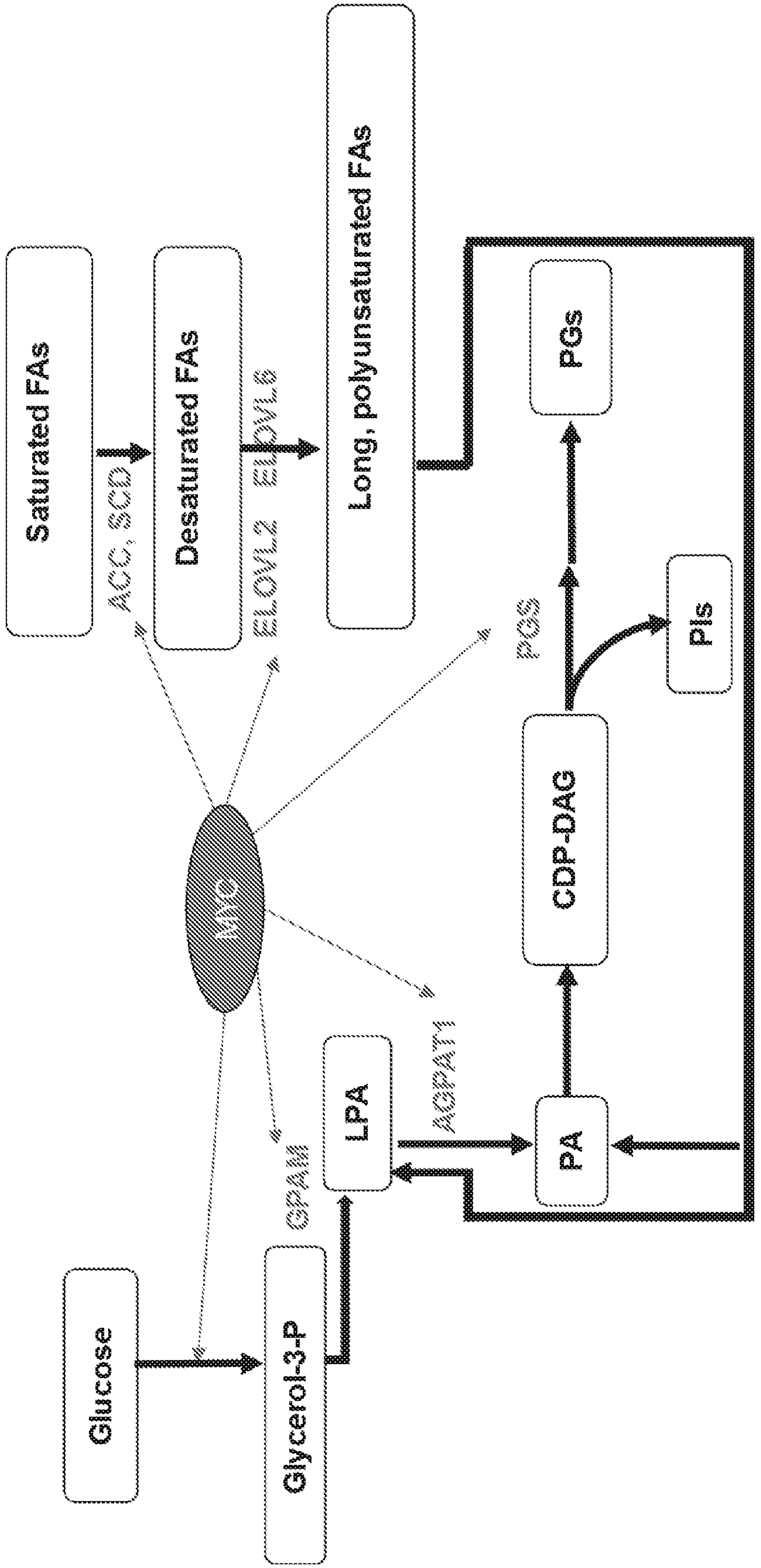
FIG. 1. MYC induces PG synthesis. Diagram showing MYC's regulation of PG synthesis genes, including GPAM or GPAT.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with cancer, e.g. those having tumors) as well as those in which prevention is desired (e.g., those with increased susceptibility to cancer; those with cancer; those suspected of having cancer; etc.).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

A "therapeutically effective amount", a "therapeutically effective dose" or "therapeutic dose" is an amount sufficient to effect desired clinical results (i.e., achieve therapeutic efficacy, achieve a desired therapeutic response, etc.). A therapeutically effective dose can be administered in one or more administrations. For purposes of this disclosure, a therapeutically effective dose of an agent that inhibits a target gene (e.g., a MYC-dependent target gene, and the like) and/or compositions is an amount that is sufficient, when administered to the individual, to palliate, ameliorate, stabilize, reverse, prevent, slow or delay the progression of the disease state (e.g., cancer, etc.) by, for example, inhibiting the growth of, inducing death of or otherwise preventing the clinical progressing of a MYC-dependent cancer present in the subject.

Glycerol-3-phosphate acyltransferase (GPAT, EC 2.3.1.15) There are four known isoforms of GPAT in humans, two microsomal isoforms located in the endoplasmic reticulum (GPAT3 and GPAT4), and two located in mitochondria (mtGPAT1 and mtGPAT2). The mitochondrial forms may be referred to as GPAM. mtGPAT1 is located on the outer mitochondrial membrane. mtGPAT1 displays a strong preference for incorporating palmitoyl-CoA (16:0), thereby primarily producing saturated phospholipids, whereas the other three enzymes are not selective. In some embodiments a GPAT inhibitor described herein selectively inhibits GPAT1.

FSG67 (2-(Nonylsulfonamido) benzoic acid) is an inhibitor of glycerol 3-phosphate acyltransferase (GPAT); $IC_{50}$=24 μM. It has been shown to reduce food intake, decrease body weight and adiposity, enhance energy utilization as fatty acid oxidation, reverse hepatic steatosis, and enhance insulin sensitivity in diet-induced obese mice. The inhibitor comprises structures with a negative charge at physiological pH to mimic the phosphate group of glycerol-3-phosphate and a long, saturated chain to mimic the chain of palmitoyl-CoA, the substrate for which GPAT1 demonstrates a strong preference. A sulfonamide linker represents a stable mimic of the presumed intermediate or transition state of the acylation reaction catalyzed by GPAT.

The term "obesity-related condition" refers to any disease or condition that is caused by or associated with (e.g., by biochemical or molecular association) obesity or that is caused by or associated with weight gain and/or related biological processes that precede clinical obesity. Examples of obesity-related conditions include, but are not limited to, type 2 diabetes, metabolic syndrome, fatty liver disease such as NASH, hyperglycemia, hyperinsulinemia, impaired glucose tolerance, impaired fasting glucose, hyperlipidemia, hypertriglyceridemia, insulin resistance, hypercholesterolemia, atherosclerosis, coronary artery disease, peripheral vascular disease, and hypertension.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias.

In some cases, the individual has recently undergone treatment for neoplasia (e.g., cancer, a tumor, etc.) and are therefore at risk for recurrence. In some instances, the individual has not recently or previously undergone treatment for a neoplasia (e.g., cancer, a tumor, etc.) but has been newly diagnosed with a neoplasia. Any and all neoplasia are suitable neoplasia to be treated by the subject methods e.g., utilizing an agent described herein or a herein described treatment kit.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent. Exemplary combinations of agents include chemotherapeutic and immune-oncology agents for the treatment of cancer; and for treatment of metabolic syndrome and related disorders, agents such as statins, ezetimibe, thiazolidinediones, GLP-1 agonists, DPP-4 inhibitors, etc.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, $10^{-16}$ M or less). "Affinity" refers to the strength of binding, increased binding affinity being correlated with a lower Kd.

The term "Alkyl" refers to a $C_1$-$C_{20}$ alkyl that may be linear, branched, or cyclic. "Lower alkyl", as in "lower alkyl", or "substituted lower alkyl", means a $C_1$-$C_{10}$ alkyl. The term "alkyl", "lower alkyl" or "cycloalkyl" includes deuterated methyl, ethyl, isopropyl, propyl, butyl, isobutyl, sec-butyl, tert-butyl, pentyl, neopentyl, hexyl, cyclopropyl, cyclobutyl, cyclopentyl, cyclopropylmethyl, cyclohexyl, cyclohexylmethyl, cyclobutylethyl, decalinyl, norboranyl, adamantanyl and related deuterocarbon moieties. In certain embodiments, the alkyl is a $C_8$-$C_{20}$ alkyl. In certain embodiments the alkyl group is poly deuterated.

A "substituted alkyl" is an alkyl which is typically mono-, di-, or tri-substituted with heterocycloalkyl, aryl, substituted aryl, heteroaryl, nitro, cyano, halo, —OR, —SR, —COR, —OC(O)R, —C(O)OR, $—NR_2$, $—N^+R_3$, $—SO_3^-$ $—SO_2OR$, $—OSO_2R$, $—SO_2NR_2$, $—NRSO_2R$, $—CONR_2$, or —NRCOR, where each R is, independently, hydrogen, lower alkyl, R'-substituted lower alkyl, aryl, R'-substituted aryl, heteroaryl, heteroaryl(alkyl), R'-substituted aryl(alkyl), or aryl(alkyl) and each R' is, independently, hydroxy, halo, alkyloxy, cyano, thio, nitro, alkyl, halo-alkyl, or amino. Substituted alkyls which are substituted with one to three of the substituents selected from the group consisting of cyano, halo, alkyloxy, thio, nitro, amino, or hydroxy are particularly of interest.

The term "Aryl" refers to an aromatic heterohydrocarbyl containing 6 to 20 ring carbon atoms, having a single ring (e.g., phenyl), or two or more condensed rings, such as 2 to 3 condensed rings (e.g., naphthyl), or two or more aromatic rings, such as 2 to 3 aromatic rings, which are linked by a single bond (e.g., biphenylyl). In certain cases, the aryl is $C_6$-$C_{16}$ or $C_6$ to $C_{14}$. In certain embodiments the alkyl group has one or more hydrogen atoms replaced with deuterium.

Heteroaryl means an aromatic ring system containing 1 to 10 ring carbon atoms and 1 to 5 heteroatoms selected from O, N, S, Se, having a single ring (e.g., thiophene, pyridine, pyrazine, imidazole, oxazole, tetrazole, etc.), or two or more condensed rings, for example 2 to 3 condensed rings (e.g., indole, benzimidazole, quinolone, quinoxaline, phenothiazine, etc.), or two or more aromatic rings, such as 2 to 3 aromatic rings, which are linked by a single bond (e.g., bipyridyl). In some cases, the heteroaryl is $C_1$-$C_{16}$, and a selection of 1 to 5 heteroatoms consisting of S, Se, N, and O.

The term Heterocycloalkyl refers to a nonaromatic ring system containing 1 to 10 ring carbon atoms and 1 to 5 heteroatoms selected from O, N, S, Se, having a single ring (e.g., tetrahydrofuran, aziridine, azetidine, pyrrolidine, piperidine, tetrathiopyran, hexamethylene oxide, oxazepane, morpholine etc.), or two or more condensed rings, such as 2 to 3 condensed rings (e.g., indoline, tetrahydrobenzodiazapines, etc. In certain cases, the heterocycloalkyl is $C_1$-$C_{16}$, and a selection of 1 to 5 heteroatoms consisting of S, Se, N, and O.

Substituted heterocycloalkyl, aryl, heteroaryl are optionally substituted with, hydrogen, 1 to 3 alkyl, alkenyl, alkynyl, cycloalkyl, cycloalkyl(alkyl), aryl, substituted aryl, aryl (alkyl), $—SO_2NR^{5'}R^{5'}$, $—PO_3H_2$, $—NR^{5'}SO_2R^6$ or $—NR^{5'}C(═O)R^6$, wherein $R^{5'}$ and $R^6$ are independently, hydrogen, alkyl, alkenyl, alkynyl, cycloalkyl, cycloalkyl(alkyl), aryl, optionally substituted heterocycloalkyl, aryloxy, heteroaryl, heteroaryl(alkyl), or $R^{5'}$ and $R^6$ together are $—(CH_2)_{3-6}—$ or $—(CH_2)_{0-3}X(CH_2)_{0-3}—$ where X═NR, O, S, $SO_2$, substituted aryl(alkyl), halo(alkyl), $SF_5$, $NR^{5'}{}_3{}^+$, azido, cyano, $—OR^{5'}$, $—SR^{5'}$, $—NR^{5'}R^6$, halogen, nitro, $SCH_3$, $OCF_3$, $SO_2CH_3$, $SCF_3$, $SO_2CF_3$, $CF_3$, $—SO_2OR^{5'}$, $—OSO_2R^{5'}$, $CCl_3$, $—C(═O)R^{5'}$, $—C(═O)OR^{5'}$; $—C(═O)NR^{5'}R^6$, $—OC(═O)R^{5'}$.

As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a substituent (e.g., as described herein).

Salts include but are not limited to: Na, K, Ca, Mg, ammonium, tetraalkyl ammonium, aryl and alkyl sulfonates, phosphates, carboxylates, sulfates, Cl, Br, and guanidinium.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "heterocycloalkyl(alkyl)" refers to the group (heterocycloalkyl)-(alkyl)-.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus, the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112. In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

Definitions of other terms and concepts appear throughout the detailed description below.

DETAILED DESCRIPTION

GPAT Inhibitors

Provided are GPAT inhibitors, of any of formulae (IA), (IB) or (IC):

(IA)

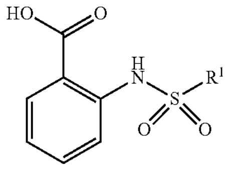

(IB)

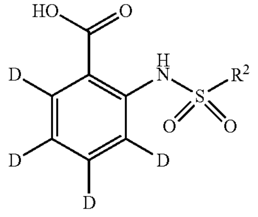

(IC)

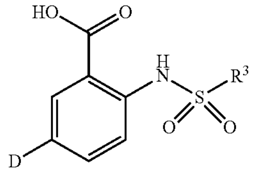

Wherein:

$R^1$ is selected from deuterated alkyl, or substituted deuterated alkyl;

$R^2$ and $R^3$ are each independently selected from alkyl, substituted alkyl, deuterated alkyl, or substituted deuterated alkyl.

In certain embodiments, $R^1$ is a deuterated alkyl. In certain embodiments of $R^1$, the deuterated alkyl is a poly deuterated alkyl. In certain embodiments, $R^2$ is a deuterated alkyl. In certain embodiments of $R^2$, the deuterated alkyl is a poly deuterated alkyl. In certain embodiments $R^2$ is alkyl. In certain embodiments, $R^3$ is a deuterated alkyl. In certain embodiments of $R^3$, the deuterated alkyl is a poly deuterated alkyl. In certain embodiments of a GPAT inhibitor of formulas (IA), $R^1$ is a deuterated $C_8$-$C_{20}$ alkyl group. In certain embodiments of $R^1$, the deuterated $C_8$-$C_{20}$ alkyl group is a poly deuterated $C_8$-$C_{20}$ alkyl group. In some embodiments, the deuterated or poly deuterated alkyl group has more than 8 carbons, such as 9, 10, 11, 12, 13, 14, 15, 16, 17, 18, 19 or 20 carbons. In some embodiments, the deuterated or poly deuterated alkyl group has 9 carbons. In some embodiments, the deuterated or poly deuterated alkyl group has 10 carbons. In some embodiments, the deuterated or poly deuterated alkyl group has 11 carbons. In some embodiments, the deuterated or poly deuterated alkyl group has 12 carbons. In some embodiments, the deuterated or poly deuterated alkyl group has 13 carbons. In some embodiments, the deuterated or poly deuterated alkyl group has 14 carbons.

In certain embodiments of a GPAT inhibitor of formulas (IB), $R^2$ is a $C_8$-$C_{20}$ alkyl group or a deuterated $C_8$-$C_{20}$ alkyl group. In certain embodiments of $R^2$, the deuterated $C_8$-$C_{20}$ alkyl group is a poly deuterated $C_8$-$C_{20}$ alkyl group. In some embodiments, the alkyl group or deuterated alkyl group has more than 8 carbons, such as 9, 10, 11, 12, 13, 14, 15, 16, 17, 18, 19 or 20 carbons. In some embodiments, the alkyl group or deuterated alkyl group has 9 carbons. In some embodiments, the alkyl group or deuterated alkyl group has 10 carbons. In some embodiments, the alkyl group or deuterated alkyl group has 11 carbons. In some embodiments, the alkyl group or deuterated alkyl group has 12 carbons. In some embodiments, the alkyl group or deuterated alkyl group has 13 carbons. In some embodiments, the alkyl group or deuterated alkyl group has 14 carbons.

In certain embodiments of a GPAT inhibitor of formulas (IC), $R^3$ is a $C_8$-$C_{20}$ alkyl group or a deuterated $C_8$-$C_{20}$ alkyl group. In some embodiments of $R^3$, the deuterated $C_8$-$C_{20}$ alkyl group is a poly deuterated $C_8$-$C_{20}$ alkyl group. In some embodiments, the alkyl group or deuterated alkyl group has more than 8 carbons, such as 9, 10, 11, 12, 13, 14, 15, 16, 17, 18, 19 or 20 carbons. In some embodiments, the alkyl group or deuterated alkyl group has 9 carbons. In some embodiments, the alkyl group or deuterated alkyl group has 10 carbons. In some embodiments, the alkyl group or deuterated alkyl group has 11 carbons. In some embodiments, the alkyl group or deuterated alkyl group has 12 carbons. In some embodiments, the alkyl group or deuterated alkyl group has 13 carbons. In some embodiments, the alkyl group or deuterated alkyl group has 14 carbons.

In certain embodiments the subject GPAT inhibitor is a compound selected from:

(1)

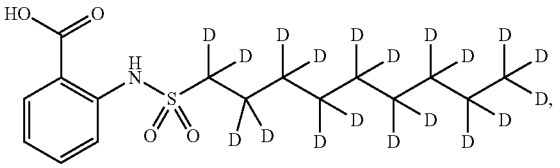

(2)

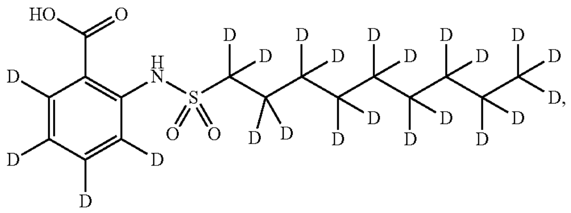

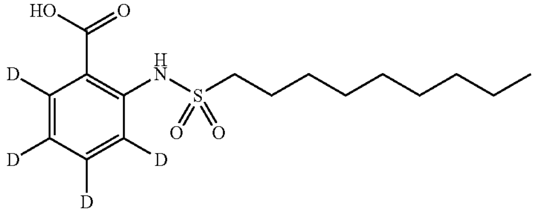

(3, also referred to herein as GFZ1.1) ,

-continued (4)

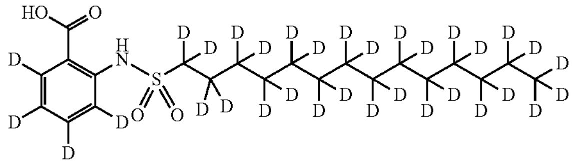

(5)

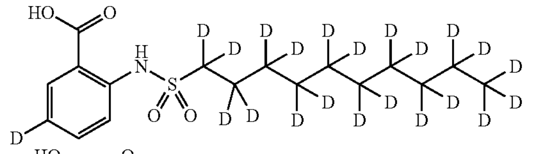

and

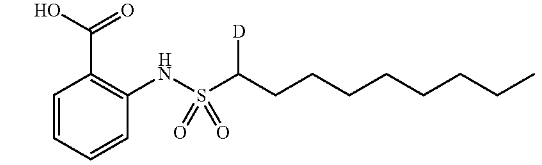

(6, also referred to herein as GFZ2)

In some cases, the subject GPAT inhibitor is of the formula (II):

(II)

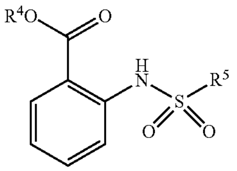

wherein:

$R^5$ is selected from alkyl, substituted alkyl, deuterated alkyl and substituted deuterated alkyl; and $R^4$ is selected from alkyl, substituted alkyl, alkenyl, alkynyl, cycloalkyl, cycloalkyl(alkyl), heterocycloalkyl, heterocycloalkyl(alkyl), aryl, substituted aryl, aryl(alkyl), substituted aryl(alkyl), halo(alkyl), heteroaryl, heteroaryl(alkyl);

or a pharmaceutically acceptable salt or solvate thereof.

In certain embodiments of a GPAT inhibitor of formula (II), $R^4$ is selected from alkyl, substituted alkyl, cycloalkyl, cycloalkyl(alkyl), heterocycloalkyl, heterocycloalkyl(alkyl), aryl, substituted aryl, aryl(alkyl), substituted aryl(alkyl), halo(alkyl), heteroaryl, heteroaryl(alkyl);

In certain embodiments of a GPAT inhibitor of formula (II), $R^4$ is selected from alkyl and substituted alkyl. In certain cases one or more substituent on the substituted alkyl is a halogen, e.g., Br, Cl, I or F. In certain cases, $R^4$ is an alkylhalide group, wherein the halide is fluoride. In certain cases, $R^4$ is an alkylhalide group, wherein the halide is chloride. In certain cases, $R^4$ is an alkylhalide group, wherein the halide is bromide. In certain cases, $R^4$ is an alkylhalide group, wherein the halide is iodide.

In certain embodiments of a GPAT inhibitor of formula (II), $R^4$ is selected from cycloalkyl, cycloalkyl(alkyl), heterocycloalkyl, and heterocycloalkyl(alkyl), wherein any of the cyclic groups are optionally substituted (e.g., with a substituent as described herein). In certain cases, $R^4$ is a cycloalkyl, e.g., including, but not limited to cyclohexane, cyclopentane. In certain cases $R^4$ is a cycloalkyl(alkyl). In certain cases, $R^4$ is a heterocycloalkyl (e.g., as described herein). In certain cases, $R^4$ is a heterocycloalkyl(alkyl).

In certain embodiments of a GPAT inhibitor of formula (II), $R^4$ is selected from aryl, aryl(alkyl), heteroaryl, and heteroaryl(alkyl), wherein any of the groups are optionally substituted (e.g. with a substituent as described herein). In certain cases, $R^4$ is an aryl group. In certain cases, $R^4$ is an aryl(alkyl). In certain cases, $R^4$ is a heteroaryl. In certain cases, $R^4$ is a heteroaryl(alkyl).

In certain embodiments of the GPAT inhibitor of formula (II), $R^4$ is of the formula (III):

(III)

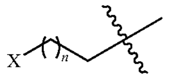

wherein:

X is selected from an amine (e.g., a primary amine, a secondary amine, a tertiary amine or a quaternary amine), a sulfonate, a heterocycloalkyl and a heteroaryl; and n is an integer from 0 to 10.

In certain embodiments of a GPAT inhibitor of formula (II), $R^4$ is selected from the group consisting of methyl, ethyl, isopropyl, polyethylene glycol (PEG),

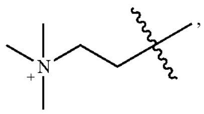

,

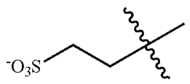

and

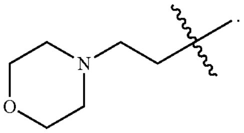

.

In certain cases, $R^4$ is methyl. In other cases, $R^4$ is ethyl. In some other cases $R^4$ is isopropyl. In certain cases, $R^4$ is PEG. In some cases, $R^4$ is an alkyl group terminating in —$N^+$Me. In some cases, $R^4$ is

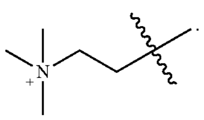

.

In some cases, $R^4$ is an alkyl group terminating in —$SO_3^-$. In some cases, $R^4$ is

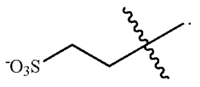

.

In some cases, $R^4$ is an alkyl group terminating in a morpholine. In some cases, the $R^4$ is

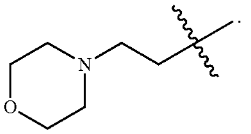

In certain embodiments of a GPAT inhibitor of formulas (II), $R^5$ is a $C_8$-$C_{20}$ alkyl group. In some embodiments, the alkyl group has more than 8 carbons, such as 9, 10, 11, 12, 13, 14, 15, 16, 17, 18, 19 or 20 carbons. In some embodiments, the alkyl group has 9 carbons. In some embodiments, the alkyl group has 10 carbons. In some embodiments, the alkyl group has 11 carbons. In some embodiments, the alkyl group has 12 carbons. In some embodiments, the alkyl group has 13 carbons. In some embodiments, the alkyl group has 14 carbons.

In certain embodiments of a GPAT inhibitor of formulas (II), $R^5$ is a $C_8$-$C_{20}$ deuterated alkyl group. In certain embodiments of $R^5$, the $C_8$-$C_{20}$ deuterated alkyl group is a $C_8$-$C_{20}$ poly deuterated alkyl group. In some embodiments, the deuterated or poly deuterated alkyl group has more than 8 carbons, such as 9, 10, 11, 12, 13, 14, 15, 16, 17, 18, 19 or 20 carbons. In some embodiments, the deuterated or poly deuterated alkyl group has 9 carbons. In some embodiments, the deuterated or poly deuterated alkyl group has 10 carbons. In some embodiments, the deuterated or poly deuterated alkyl group has 11 carbons. In some embodiments, the deuterated or poly deuterated alkyl group has 12 carbons. In some embodiments, the deuterated or poly deuterated alkyl group has 13 carbons. In some embodiments, the deuterated or poly deuterated alkyl group has 14 carbons.

In certain embodiments of a GPAT inhibitor of formula (II), $R^5$ is a $C_8$-$C_{20}$ substituted alkyl group.

In certain embodiments of a GPAT inhibitor of formulas (II), the structure is a compound selected from:

(7)

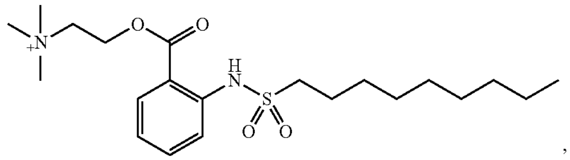

, (8)

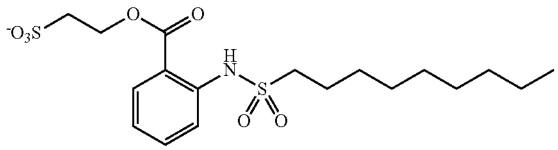

(9)

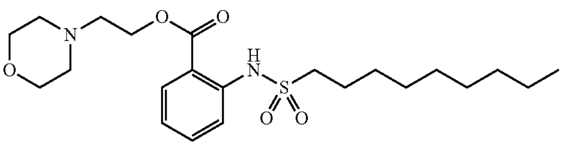

-continued

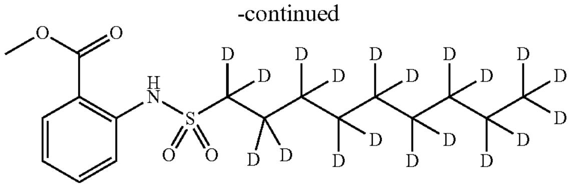

(10, also referred to herein as GFZ1.2) and

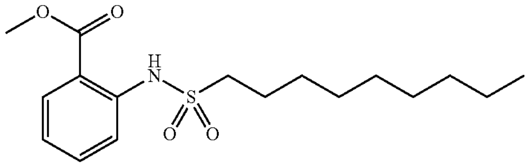

(11, also referred to herein as GFZ1.5) .

In certain embodiments, the GPAT inhibitor compound is described by the structure of one of the compounds of formulae (IA), (IB), (IC) or (II) or structures 1-11. It is understood that any of the subject compounds disclosed herein may be present in a salt form. In some cases, the salt form of the compound is a pharmaceutically acceptable salt.

Aspects of the present disclosure include GPAT inhibitor compounds (e.g., as described herein), salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject GPAT inhibitor compounds, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid. In certain embodiments salts include, but are not limited to sodium, potassium, calcium, magnesium, ammonium, tetraalkyl ammonium, aryl and alkyl sulfonates, phosphates, carboxylates, sulfates, chloride, bromide, and guanidinium.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the promoiety is attached to the carboxylic acid group of the subject compounds. In certain cases, the promoiety is an acyl or substituted acyl group. In certain cases, the promoiety is an alkyl or substituted alkyl group, e.g., that forms an ester functional group when attached to the carboxylic acid group of the subject compounds.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include byway of example, water, methanol, ethanol, isopropanol, acetic acid, and the like. When the solvent is water, the solvate formed is a hydrate.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

The subject GPAT inhibitors comprise one or more deuterium substitutions for hydrogen, which may provide for enhanced pharmacokinetic/pharmacodynamic properties of the molecule relative to its non-deuterated form. These improved features may include, without limitation, increased drug exposure, reduced dosing, slowed clearance, improved efficacy and reduced safety liabilities. The $IC_{50}$ of the GPAT inhibitor may be less than 100 μM, such as less than 90 μM, less than 80 μM, less than 70 μM, less than 60 μM, less than 50 μM, less than 40 μM, less than 30 μM, less than 20 μM, or even less. In certain embodiments, the $IC_{50}$ of the GPAT inhibitor may be less about 24 μM, e.g. less than about 10 μM, less than about 5 μM, less than about 1 μM.

Formulations and Dosing

The compounds of this disclosure can be supplied in the form of a pharmaceutical composition. Any suitable pharmaceutical composition may be employed, described in more detail below. As such, in some instances, methods of the present disclosure may include administering an inhibitor in a composition comprising an excipient (e.g., an isotonic excipient) prepared under sufficiently sterile conditions for administration to a mammal, e.g., a human.

Administration of an inhibitor to a subject, as described herein, may be performed employing various routes of administration. The route of administration may be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intratumoral (it), intraperitoneal (ip), rectal, topical, ophthalmic, nasal, subcutaneous, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated.

Therapeutically effective doses of a subject compound or pharmaceutical composition can be determined by one of skill in the art, with a goal of achieving local (e.g., tissue) concentrations that are at least as high as the $IC_{50}$ of an applicable compound disclosed herein.

In some embodiments, an effective amount of a compound is an amount that ranges from about 50 ng/ml to about 50 μg/ml (e.g., from about 50 ng/ml to about 40 μg/ml, from about 30 ng/ml to about 20 μg/ml, from about 50 ng/ml to about 10 μg/ml, from about 50 ng/ml to about 1 μg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 μg, from about 1 μg to about 10 μg, from about 10 μg to about 50 μg, from about 50 μg to about 150 μg, from about 150 μg to about 250 μg, from about 250 μg to about 500 μg, from about 500 μg to about 750 μg, from about 750 μg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

In some embodiments, a single dose of a compound is administered. In other embodiments, multiple doses are administered. Where multiple doses are administered over a period of time, the compound can be administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Conversion of an animal dose to human equivalent doses (HED) may, in some instances, be performed using the conversion table and/or algorithm provided by the U.S. Department of Health and Human Services, Food and Drug Administration, Center for Drug Evaluation and Research (CDER) in, e.g., *Guidance for Industry: Estimating the Maximum Safe Starting Dose in Initial Clinical Trials for Therapeutics in Adult Healthy Volunteers* (2005) Food and Drug Administration, 5600 Fishers Lane, Rockville, Md. 20857, the disclosure of which is incorporated herein by reference).

A pharmaceutical composition comprising a subject compound (i.e., a GPAT inhibitory agent or a combination thereof) may be administered to a patient alone, or in combination with other supplementary active agents. The pharmaceutical compositions may be manufactured using any of a variety of processes, including, without limitation, conventional mixing, dissolving, granulating, dragee-making, levigating, solid dispersions, emulsifying, encapsulating, entrapping, spray drying, micronizing, electrospraying and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitol monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline: (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified, or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. In some instances, a topical preparation of a medicament useful in the methods described herein may include, e.g., an ointment preparation that includes one or more excipients including, e.g., mineral oil, paraffin, propylene carbonate, white petrolatum, white wax and the like, in addition to one or more additional active agents.

Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Exemplary treatment regimens include, but are not limited to, administration via injection to achieve a dose of from about 0.1 μg/kg to about 100 mg/kg or from about 1 μg/kg to about 10 mg/kg of the compound of the present disclosure. Other exemplary treatment regimens include, but are not limited to, administration via injection to achieve a dose of from about 1 μg/day to about 100 mg/day or from about 500 μg/day to about 2000 mg/day of the compound of the present disclosure in a single or divided dose. Still other exemplary treatment regimens include, but are not limited to, pulmonary administration; nasal administration; and buccal administration. An initial target plasma concentration may range from about 1 pM to about 1000 pM. Guidance as to particular dosages and methods of delivery is generally available to practitioners in the art and is provided herein.

Methods of Use

The GPAT inhibitors described herein find use in the treatment of cancer in mammals. In some embodiments, the subject GPAT inhibitors find use in the treatment of cancer in humans. Methods of treating a subject may include administering to the subject an effective amount of the GPAT inhibitor compound. In some embodiments the cancer is a MYC-driven cancer. In some embodiments a subject is pre-screened to determine if the cancer is lipogenesis-dependent, for example by comparing a lipogenesis profile obtained from a subject having a neoplasm with a reference lipogenesis profile to classify whether the neoplasm is lipogenesis-dependent.

The provided methods may find use with subjects having a variety of different neoplasms. Relevant cancers include tumors (e.g., solid tumors (e.g., sarcomas and carcinomas) and blood cancers. Non-limited examples of various cancers to which the subject methods may be applied include: Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, HeartCancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Orpharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like.

In some instances, a subject to which the provided methods may be applied may be a subject having a hematological (i.e., blood) cancer, e.g., a leukemia or a lymphoma. Non-limiting examples of hematological cancers include: Acute Lymphoblastic Leukemia, Adult: Acute Lymphoblastic Leukemia, Childhood; Acute Myeloid Leukemia, Adult; Acute Myeloid Leukemia, Childhood; Chronic Lymphocytic Leukemia; Chronic Myelogenous Leukemia; Hairy Cell Leukemia; AIDS-Related Lymphoma; Cutaneous T-Cell Lymphoma (see Mycosis Fungoides and the Sezary Syndrome); Hodgkin Lymphoma, Adult; Hodgkin Lymphoma, Childhood: Hodgkin Lymphoma During Pregnancy; Mycosis Fungoides; Non-Hodgkin Lymphoma, Adult; Non-Hodgkin Lymphoma, Childhood; Non-Hodgkin Lymphoma During Pregnancy; Primary Central Nervous System Lymphoma; Sézary Syndrome; T-Cell Lymphoma, Cutaneous (see Mycosis Fungoides and the Sezary Syndrome); Waldenström Macroglobulinemia (see Non-Hodgkin Lymphoma) Chronic Myeloproliferative Neoplasms; Langerhans Cell Histiocytosis; Multiple Myeloma/Plasma Cell Neoplasm; Myelodysplastic Syndromes; Myelodysplastic/Myeloproliferative Neoplasms; and the like.

In some instances, a subject to which the provided methods may be applied may be a subject having a carcinoma (e.g., an adenocarcinoma or a squamous cell carcinoma). Non-limiting examples of carcinomas include: acinar carcinoma, acinic cell carcinoma, acinous carcinoma, adenocystic carcinoma, adenoid cystic carcinoma, adenosquamous carcinoma, adnexal carcinoma, adrenocortical carcinoma, alveolar carcinoma, ameloblastic carcinoma, apocrine carcinoma, basal cell carcinoma, bronchioloalveolar carcinoma, bronchogenic carcinoma, cholangiocellular carcinoma, chorionic carcinoma, clear cell carcinoma, colloid carcinoma, colorectral carcinoma, cribriform carcinoma, ductal carcinoma in situ, embryonal carcinoma, carcinoma en cuirasse, endometrioid carcinoma, epidermoid carcinoma, carcinoma ex mixed tumor, carcinoma ex pleomorphic adenoma, follicular carcinoma of thyroid gland, hepatocellular carcinoma, carcinoma in situ, intraductal carcinoma, Hürthle cell carcinoma, inflammatory carcinoma of the breast, large cell carcinoma, invasive lobular carcinoma, lobular carcinoma, lobular carcinoma in situ (LCIS), medullary carcinoma, meningeal carcinoma, Merkel cell carcinoma, mucinous carcinoma, mucoepidermoid carcinoma, nasopharyngeal carcinoma, non-small cell carcinoma, non-small cell lung carcinoma (NSCLC), oat cell carcinoma, papillary carcinoma, renal cell carcinoma, scirrhous carcinoma, sebaceous carcinoma, carcinoma simplex, signet-ring cell carcinoma, small cell carcinoma, small cell lung carcinoma, spindle cell carcinoma, squamous cell carcinoma, terminal duct carcinoma, transitional cell carcinoma, tubular carcinoma, verrucous carcinoma, and the like.

Methods of the present disclosure may find use in analyzing and/or treating various cancers including but not limited to e.g., liver cancers, kidney cancers, blood cancer (e.g., lymphoma), lung cancers, etc. In some instances, the subject methods find use in analyzing and/or treating MYC-induced renal cell carcinoma (RCC). In some instances, the subject methods find use in analyzing and/or treating MYC-induced T-cell lymphoma (T-ALL). In some instances, the subject methods find use in analyzing and/or treating MYC-induced lung cell carcinoma. In some instances, the subject methods find use in analyzing and/or treating MYC-induced hepatocellular carcinoma (HCC). In some instances, the subject cancers may be MYC driven cancers. In some instances, the cancers may be cancers in which MYC induces fatty acid synthesis and/or the expression of fatty acid synthesis genes.

In certain embodiments the present disclosure provides compositions and methods of treating hepatic cancers. The methods involve administering the subject compound, as described above to a subject with a hepatic cancer, for a period of time sufficient to inhibit growth of the hepatic cancer. An effective amount of a compound is one that inhibits the growth of the hepatic cancer by at least about 10%, at least about 20%, at least about 25%, at least about 30%, at least about 35%, at least about 40%, at least about 45%, at least about 50%, at least about 55%, at least about 60%, at least about 65%, at least about 70%, or more. Whether the growth of the hepatic cancer is inhibited can be determined in, e.g., study groups, where individuals treated according to the subject methods have reduced incidence of hepatic cancer.

In other embodiments, methods are provided for treatment of conditions relating to obesity and metabolic syndrome, including without limitation Type II diabetes mellitus, metabolic syndrome, hyperlipidemia and fatty liver disease. An effective dose of a GPAT inhibitor is administered to achieve a reduction in the symptoms of the disease.

Type II diabetes mellitus is characterized by insulin resistance and hyperglycemia, which in turn can cause retinopathy, nephropathy, neuropathy, or other morbidities. Additionally, diabetes is a well-known risk factor for atherosclerotic cardiovascular disease. Metabolic syndrome refers to a group of factors, including hypertension, obesity, hyperlipidemia, and insulin resistance (manifesting as frank diabetes or high fasting blood glucose or impaired glucose tolerance), that raises the risk of developing heart disease, diabetes, or other health problems; (Grundy et al, Circulation. 2004; 109:433-438). There is a well-characterized progression from normal metabolic status to a state of impaired fasting glucose (IFG: fasting glucose levels greater than 100 mg/dL) or to a state of impaired glucose tolerance (IGT: two-hour glucose levels of 140 to 199 mg/dL after a 75 gram oral glucose challenge). Both IFG and IGT are considered pre-diabetic states, with over 50% of subjects with IFG progressing to frank type II diabetes within, on average, three years (Nichols, Diabetes Care 2007. (2): 228-233). The insulin resistance is caused, at least in part, by chronic low-grade inflammation (Romeo G R et al, Arterioscler Thromb Vasc Biol. 2012 32(8):1771-6; de Luca C et al, FEBS Lett. 2008 582(1):97-105; Ma K et al, Diabetes Metab Res Rev. 2012 28(5):388-94). Macrophages accumulate in obese adipose tissue, where they produce TNF and other inflammatory cytokines in response to stimulation with saturated fatty acids and circulating lipopolysaccharide (LPS) (Johnson et al, Cell 2013. 152(4):673-84; Bhargava P et al, Biochem J. 2012 442(2):253-62). Moreover, TNF inhibition can abrogate insulin resistance (Johnson et al, Cell 2013. 152(4):673-84).

Hyperlipidemia may also be treated. Hyperlipidemia involves abnormally elevated levels of any or all lipids and/or lipoproteins in the blood. The term lipids includes: cholesterol and triglycerides. There are many different types of lipid (also called lipoproteins). Blood tests can measure the levels of lipoproteins. The standard lipid blood tests include a measurement of total cholesterol, LDL (low density lipoproteins) and HDL (high density lipoproteins), and triglycerides.

Non-alcoholic fatty liver disease (NAFLD) and non-alcoholic steatohepatitis (NASH) are conditions associated with fatty infiltration of the liver. NAFLD is one cause of a fatty liver, occurring when fat is deposited (steatosis) in the liver not due to excessive alcohol use (Clark J M et al, J. American Medical Association 289 (22): 3000-4, 2003). It can be related to insulin resistance and the metabolic syndrome and may respond to treatments originally developed for other insulin-resistant states (e.g. diabetes mellitus type 2) such as weight loss, metformin and thiazolidinediones.

NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become NASH, a state in which steatosis is combined with inflammation and fibrosis. NASH is a progressive disease: over a 10-year period, up to 20% of patients with NASH will develop cirrhosis of the liver, and 10% will suffer death related to liver disease. NASH is the most extreme form of NAFLD, and is regarded as a major cause of cirrhosis of the liver of unknown cause (McCulough A J et al, Clinics in Liver Disease 8 (3): 521-33, 2004).

Common findings in NAFLD and NASH are elevated liver enzymes and a liver ultrasound showing steatosis. An ultrasound may also be used to exclude gallstone problems (cholelithiasis). A liver biopsy (tissue examination) is the only test widely accepted as definitively distinguishing NASH from other forms of liver disease and can be used to assess the severity of the inflammation and resultant fibrosis (Adams L A et al, Postgrad Med J 82(967):315-22, 2006). Non-invasive diagnostic tests have been developed, such as FibroTest, that estimates liver fibrosis, and SteatoTest, that estimates steatosis, however their use has not been widely adopted (McCulough A J et al, Clinics in Liver Disease 8 (3): 521-33, 2004).

Screening Methods

In some embodiments, the methods of the present disclosure include treating a subject for a neoplasm by administering the subject an effective amount of one or more inhibitors of GPAT. The neoplasm may be screened prior to treatment to determine if the cancer is lipogenesis-dependent. In some aspects, methods of the present include the use of a lipogenesis profile. By "lipogenesis profile" is meant a representation of the lipids or a subset thereof present in a cellular sample (e.g., a cell, a population of cells, a tissue, an organ, etc.) which may or may include quantification of the absolute or relative amounts of the subject lipids or subset thereof. In some instances, a lipid profile or a lipogenesis profile may be obtained for glycerophospholipids or a subset thereof. Lipogenesis profiles may be compared. In some instances, a lipogenesis profile may be compared to a control (e.g., a normal tissue, a MYC "ON" control, a MYC "OFF" control, or the like). In some instances, a lipogenesis profile may be compared to a reference lipogenesis profile, e.g., a reference lipogenesis profile obtained from a control (e.g., a normal tissue reference lipogenesis profile, a MYC "ON" control reference lipogenesis profile, a MYC "OFF" control reference lipogenesis profile, or the like). In some instances, a lipogenesis profile may be employed to assign a particular lipogenesis state to a cellular sample (e.g., a cellular sample of a neoplasm, such as an RCC). Assigning a particular lipogenesis state to a cellular sample may include classifying the cellular sample as lipogenesis-dependent, e.g., when the lipogenesis profile obtained includes increased glycerophosphoglycerols as compared to a reference lipogenesis profile or decreased glycerophosphoinositols compared to the reference lipogenesis profile.

Any convenient method may be employed for obtaining a lipogenesis profile of the present methods. In some aspects, the methods of the present disclosure may include lipogenesis profiles obtained using mass spectrometry (MS) and as such may be mass spectrometry (MS) lipogenesis profiles. Any convenient and appropriate MS technology may be employed, including but not limited to e.g., desorption electrospray ionization mass spectrometry imaging (DESI-MSI).

In some instances, methods of treating a subject may include administering to the subject an effective amount of a GPAT inhibitor, when the neoplasm of the subject is classified as lipogenesis-dependent, to treat the subject for the lipogenesis-dependent neoplasm.

In some instances, a subject method of screening may include assessing the effectiveness of the candidate agent, including e.g., measuring one or more aspect of a neoplasm contacted with the agent. For example, in some instances, the screening method may include identifying the candidate agent as a MYC-driven neoplasm therapeutic agent when the MYC-driven neoplasm regresses following contacting with the agent. In some instances, a measured decrease in lipogenesis may be observed, including e.g., a decrease in glycerophosphoglycerols. In some instances, a measured increase in lipogenesis may be observed, including e.g., an increase in in glycerophosphoinositols. Such increases and decreases may be compared to one or more controls.

Kits

Also provided are kits for use in the subject methods. The subject kits may include any combination of components (e.g., therapeutic compounds, etc.) for performing the subject methods, such as e.g., methods of treating a subject for a neoplasm and/or methods of identifying a MYC-driven neoplasm. The subject kits may include a combination of agents for use in treating a subject, i.e., a "treatment kit". The subject kits may include cell lines (e.g., cell lines for use in screening) which may include neoplastic cell lines (e.g., tumor cell lines, cancer cell lines, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit or cell line(s), in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Additional Embodiments

Additional embodiments are set forth in the following clauses.

Clause 1. A GPAT inhibitor of one of formulae (IA), (IB), (IC) or (II):

(IA)

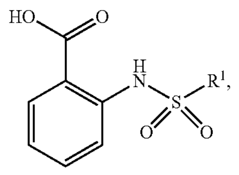

(IB)

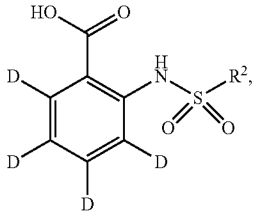

(IC)

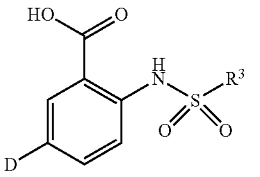

or (II)

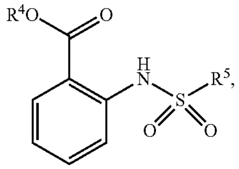

wherein:

$R^1$ is selected from deuterated alkyl and substituted deuterated alkyl;

$R^2$, $R^3$ and $R^5$ are each independently selected from alkyl, substituted alkyl, deuterated alkyl and substituted deuterated alkyl;

$R^4$ is selected from alkyl, substituted alkyl, alkenyl, alkynyl, cycloalkyl, cycloalkyl(alkyl), heterocycloalkyl, heterocycloalkyl(alkyl), aryl, substituted aryl, aryl(alkyl), substituted aryl(alkyl), halo(alkyl), heteroaryl, heteroaryl(alkyl);

or a pharmaceutically acceptable salt or solvate thereof.

Clause 2. The GPAT inhibitor of clause 1, wherein the compound is of the formula (IA) and $R^1$ is a deuterated alkyl.

Clause 3. The GPAT inhibitor of clause 2, wherein $R^1$ is a poly deuterated alkyl.

Clause 4. The GPAT inhibitor of claim 2 or 3, wherein the $R^1$ group has 8 or more carbons.

Clause 5. The GPAT inhibitor of clause 4, wherein $R^1$ is a deuterated or poly deuterated $C_9$-$C_{14}$ alkyl.

Clause 6. The GPAT inhibitor of clause 1, wherein the compound is of the formula (IB) and $R^2$ is selected from a deuterated alkyl or an alkyl group.

Clause 7. The GPAT inhibitor of clause 6, wherein $R^2$ is a poly deuterated alkyl.

Clause 8. The GPAT inhibitor of clause 6, wherein $R^2$ is an alkyl group.

Clause 9. The GPAT inhibitor of any one of clauses 6 to 8, wherein the $R^2$ group has 8 or more carbons.

Clause 10. The GPAT inhibitor of clause 9, wherein $R^2$ is a $C_9$-$C_{14}$ alkyl group or a deuterated $C_9$-$C_{14}$ alkyl group.

Clause 11. The GPAT inhibitor of clause 10, wherein $R^2$ is a $C_9$-$C_{14}$ alkyl.

Clause 12. The GPAT inhibitor of clause 1, wherein the compound is of the formula (IC) and $R^3$ is selected from a deuterated alkyl or an alkyl group.

Clause 13. The GPAT inhibitor of clause 12, wherein $R^3$ is a poly deuterated alkyl.

Clause 14. The GPAT inhibitor of clause 12, wherein $R^3$ is an alkyl group.

Clause 15. The GPAT inhibitor of any one of clauses 12 to 14, wherein the $R^3$ group has 8 or more carbons.

Clause 16. The GPAT inhibitor of clause 15, wherein $R^3$ is a $C_9$-$C_{14}$ alkyl group or a deuterated $C_9$-$C_{14}$ alkyl group.

Clause 17. The GPAT inhibitor of claim 16, wherein R is a $C_9$-$C_{14}$ deuterated alkyl.

Clause 18. The GPAT inhibitor of clause 1, wherein the compound is of the formula (II) and $R^5$ is selected from a deuterated alkyl or an alkyl group.

Clause 19. The GPAT inhibitor of clause 18, wherein $R^5$ is a poly deuterated alkyl.

Clause 20. The GPAT inhibitor of clause 18, wherein $R^5$ is an alkyl group.

Clause 21. The GPAT inhibitor of anyone of clauses 18 to 20, wherein the $R^5$ group has 8 or more carbons.

Clause 22. The GPAT inhibitor of clause 21, wherein $R^5$ is a $C_9$-$C_{14}$ alkyl group or a deuterated $C_9$-$C_{14}$ alkyl group.

Clause 23. The GPAT inhibitor of clause 1, wherein the compound is of the formula (II) and $R^4$ is selected from alkyl, substituted alkyl, cycloalkyl, cycloalkyl(alkyl), heterocycloalkyl, heterocycloalkyl(alkyl), aryl, substituted aryl, aryl(alkyl), substituted aryl(alkyl), halo(alkyl), heteroaryl, heteroaryl(alkyl).

Clause 24. The GPAT inhibitor of clause 23, wherein $R^4$ is selected from alkyl, substituted alkyl and halo(alkyl).

Clause 25, The GPAT inhibitor of clause 24, wherein $R^4$ is selected substituted alkyl.

Clause 26. The GPAT inhibitor of clause 23, wherein $R^4$ is selected from cycloalkyl, cycloalkyl(alkyl), heterocycloalkyl, and heterocycloalkyl(alkyl).

Clause 27. The GPAT inhibitor of clause 26, wherein $R^4$ is selected from heterocycloalkyl, and heterocycloalkyl(alkyl).

Clause 28. The GPAT inhibitor of clause 23, wherein $R^4$ is selected from aryl, substituted aryl, aryl(alkyl), substituted aryl(alkyl), heteroaryl, and heteroaryl(alkyl).

Clause 29. The GPAT inhibitor of clause 28, wherein $R^4$ is selected from heteroaryl, and heteroaryl(alkyl).

Clause 30. The GPAT inhibitor of clause 23, wherein $R^4$ is selected from methyl, ethyl, isopropyl, PEG,

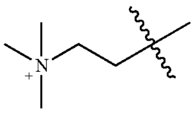
,
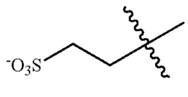
and

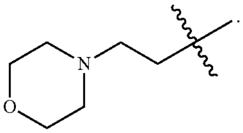 [SMILES: *CCN1CCOCC1]
.

Clause 31. The GPAT inhibitor of any one of clauses 1 to 30, selected from the compounds:

(1)

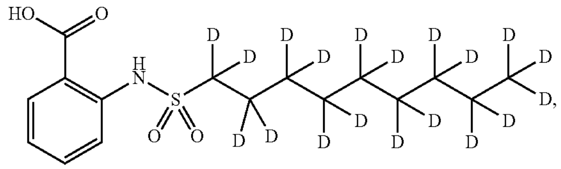

(2)

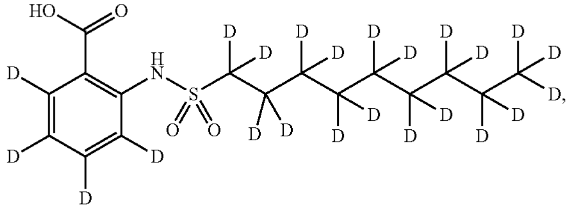

(3)

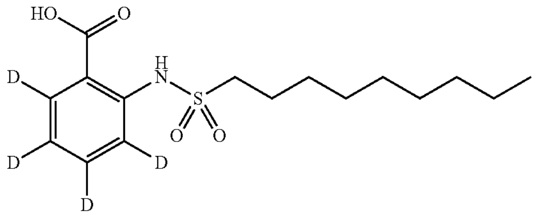

(4)

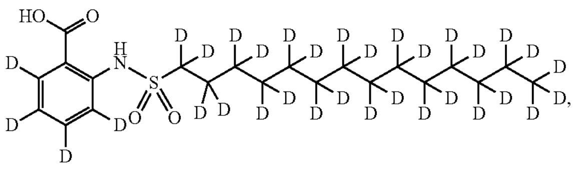

(5)

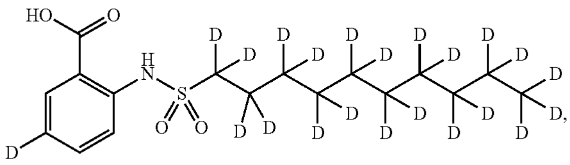

(6)

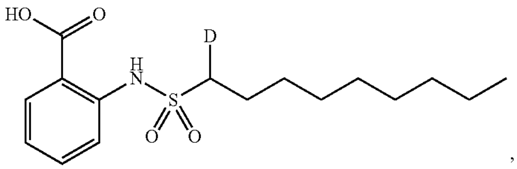
, (7)

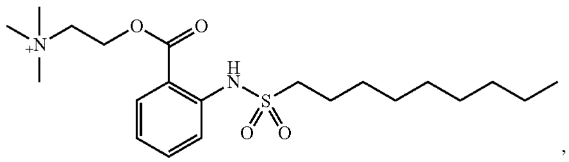
,

-continued (8)

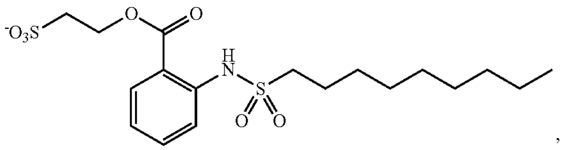

, (9)

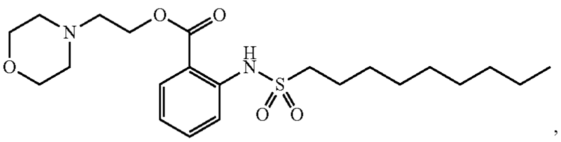

, (10)

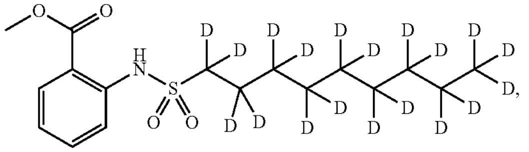

and (11)

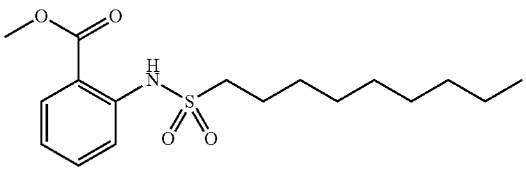

.

Clause 32. A pharmaceutical composition, comprising:

a GPAT inhibitor of any one of clauses 1-31; and a pharmaceutically acceptable excipient.

Clause 33. A method of treating a subject for cancer, the method comprising:

administering an effective dose of a GPAT inhibitor according to any of clauses 1-31 for a period of time sufficient to inhibit growth of the cancer.

Clause 34. The method of clause 33, wherein the cancer is a MYC-dependent cancer.

Clause 35. The method of clause 33 or 34, wherein the cancer is selected from renal cell carcinoma, hepatocellular carcinoma, and lymphoma.

Clause 36. The method of clause 33 or 34, wherein the cancer is a hepatic cancer.

Clause 37. The method of clause 33, wherein the cancer is a lipogenesis-dependent neoplasm.

Clause 38. The method of clause 37, comprising:

comparing a lipogenesis profile obtained from a subject having a neoplasm with a reference lipogenesis profile to classify whether the neoplasm is lipogenesis-dependent; and administering to the subject an effective amount of a GPAT inhibitor of any one of clauses 1-31, when the neoplasm is classified as lipogenesis-dependent, to treat the subject for the lipogenesis-dependent neoplasm.

Clause 39. The method of any one of clauses 33 to 38, wherein the subject is a mammal.

Clause 40. The method of clause 39, wherein the mammal is a human.

Clause 41. A method of treating a metabolic syndrome related disease, the method comprising:

administering to a subject an effective dose of a GPAT inhibitor according to any of clauses 1-31 for a period of time sufficient to reduce symptoms of the disease in the subject.

Clause 42. The method of clause 41, wherein the disease is selected from hyperlipidemia, metabolic syndrome, type 2 diabetes, fatty liver disease and obesity.

Clause 43. The method of clause 42, wherein the disease is obesity.

Clause 44. The method of any one of clauses 41 to 43, wherein the subject is a mammal.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (pl); seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); KHMSA=Potassium bis(trimethylsilyl) amide, TBAF=Tetra-n-butylammonium fluoride, DMAP=4-Dimethylaminopyridine, TEA=triethylamine, and the like.

Example 1—Exemplary Synthetic Schemes

Synthesis: Compounds may be synthesized using any convenient method. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). Reactions may be monitored by thin layer chromatography (TLC), LC/MS and reaction products characterized by LC/MS and $^1$H NMR. Intermediates and final products may be purified by silica gel chromatography or by HPLC.

The synthesis of an exemplary GPAT inhibitor, which can be adapted for the synthesis of subject compounds, is set out below:

A) Deuteration of an Exemplary Aromatic Ring.

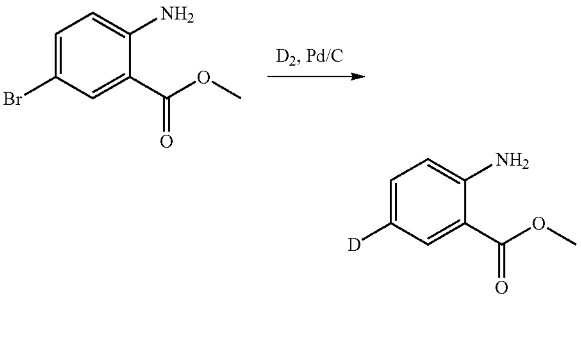

B) Preparation of an Exemplary Poly Deuterated Alkyl Group.
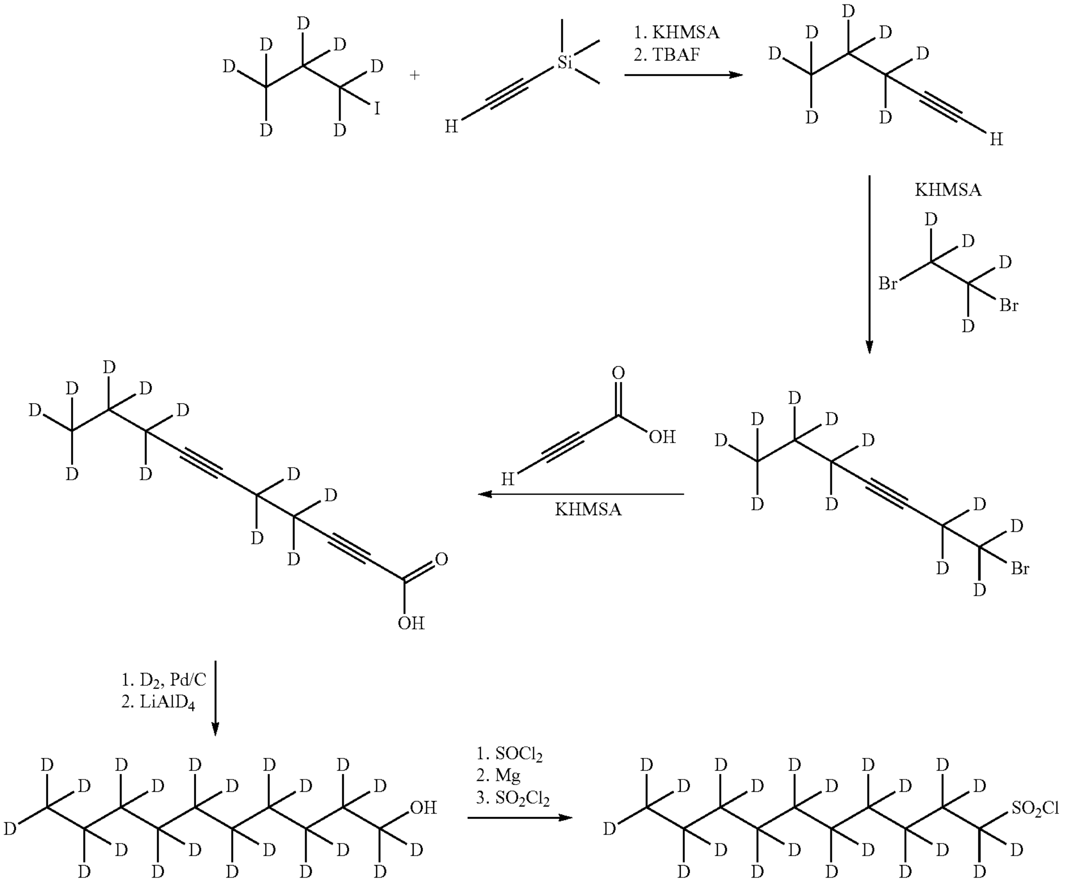
C) Preparation of Exemplary GPAT Inhibitor
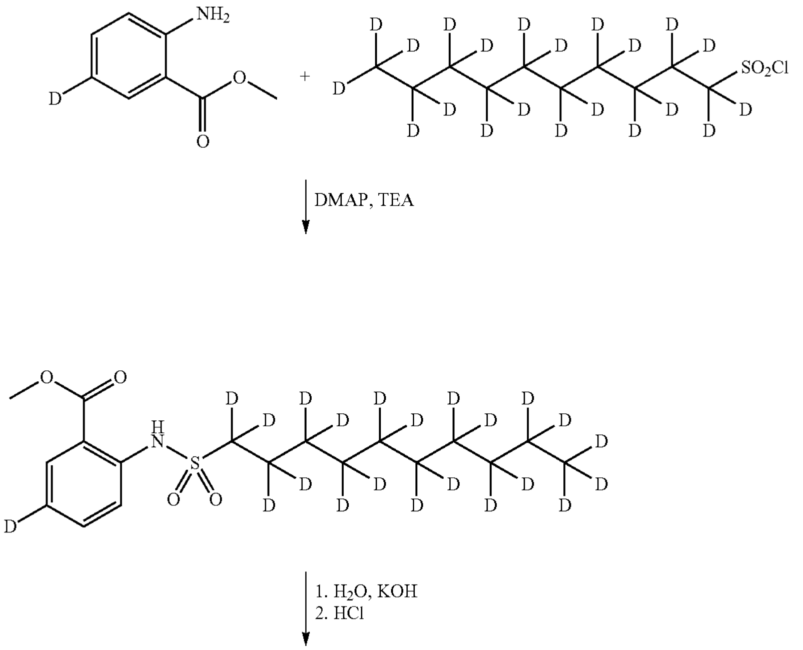

-continued

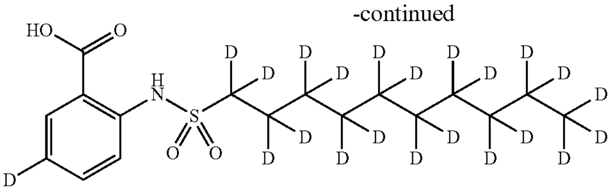

(5)

Example 2

We present a comprehensive overview of how the MYC oncogene controls lipogenesis to promote tumorigenesis. We find that MYC globally regulates the expression of key genes and their resulting proteins and metabolites in lipogenesis for human and murine cell lines as well as for transgenic mouse models. By gene expression analysis, nuclear run-on, $^{13}$C-isotope labeling, and chromatin immuno-precipitation, MYC in conjunction with a Sterol Regulatory Element-Binding Protein 1 (SREBP1) was found to induce the nonlinear expression of fatty acid biosynthesis pathway genes including Acetyl-CoA Carboxylase A (ACACA), Fatty Acid Synthase (FASN), and Stearoyl-CoA Desaturase (SCD) and to drive fatty acid chain elongation from glucose and glutamine. Desorption electrospray ionization mass spectrometric imaging (DESI-MSI) from tissue samples of several conditional transgenic mouse models identified in vivo metabolic changes in simple fatty acids and in complex phospholipids induced by MYC. Thus, MYC not only increased oleate abundance in multiple tumors, but also notably elevated the abundances of phosphatidylglycerols with elongation of fatty acid side chains and concomitant suppression of phosphatidylinositol abundances in a transgenic renal cell carcinoma model. Long, polyunsaturated fatty acids were also notably higher in abundance with prolonged MYC activation. Strong correlation between these in situ changes and elevation of gene expressions of cytidinediphosphate diacylglycerol pathway genes as well as fatty acid elongase genes were found. By administering FSG67, which inhibits GPAT, MYC-induced tumorigenesis was blocked, metabolic changes were suppressed, and tumors regressed in xenograft and primary mouse models. These results expose the vulnerability of MYC-induced cancers to inhibition of GPAT, thereby providing a therapeutic approach to treatment.

Our results suggest that MYC induced tumors are dependent on lipogenesis and phospholipid synthesis. MYC induced human tumors may be highly sensitive to inhibition of phospholipid synthesis. There is an emerging general model, that MYC orchestrates the orderly activation of glycolysis, glutaminolysis, phospholipid and fatty acid synthesis, providing a means for the balanced acquisition of nutrients and stoichiometric production of cellular biomass. For a normal cell, this is essential to enable the coordination between coordinating the need for energy metabolism and generating building blocks for biomass generation. MYC's regulation of lipid metabolism similarly is required to coordinate the respective requirements for energy, signaling molecules and membrane production. For a cancer cell, MYC overexpression provides the ability to maximize unrestrained growth but at the expense of a remarkable vulnerability to the inhibition of key regulators of this pathway.

Figure 2:
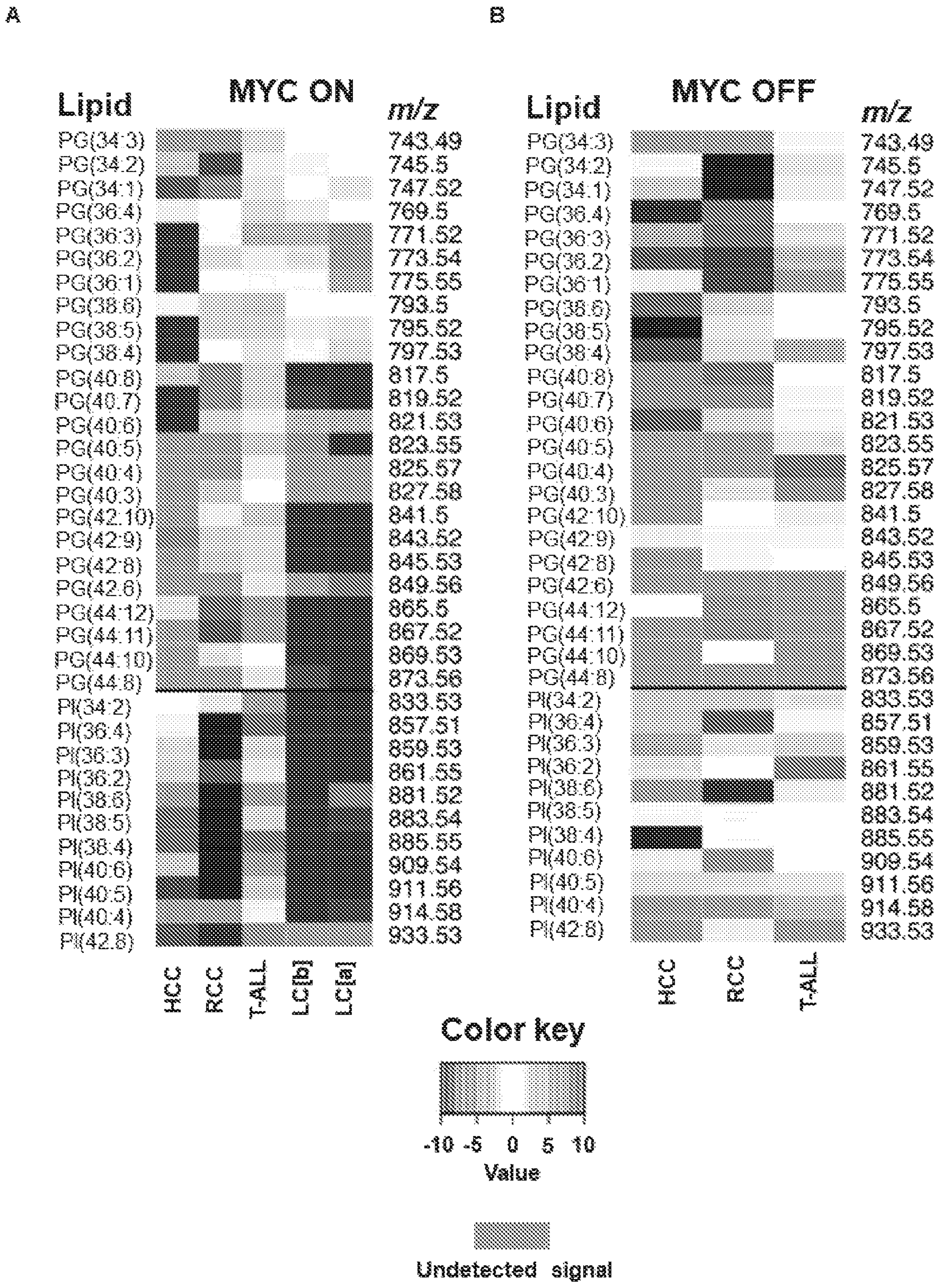
FIG. 2, panels A and B. Lipid signature of MYC-induced HCC, RCC, T-ALL, LC bronchiolar (b), and adenoma (a). PG and PI relative expression in MYC ON state compared to normal tissue for HCC, RCC, T-ALL, LC (b), and LC (a). PG and PI relative expression in MYC OFF state compared to MYC ON in HCC, RCC, and T-ALL. Pale gray color represents undetected ion signal.
Figure 3:
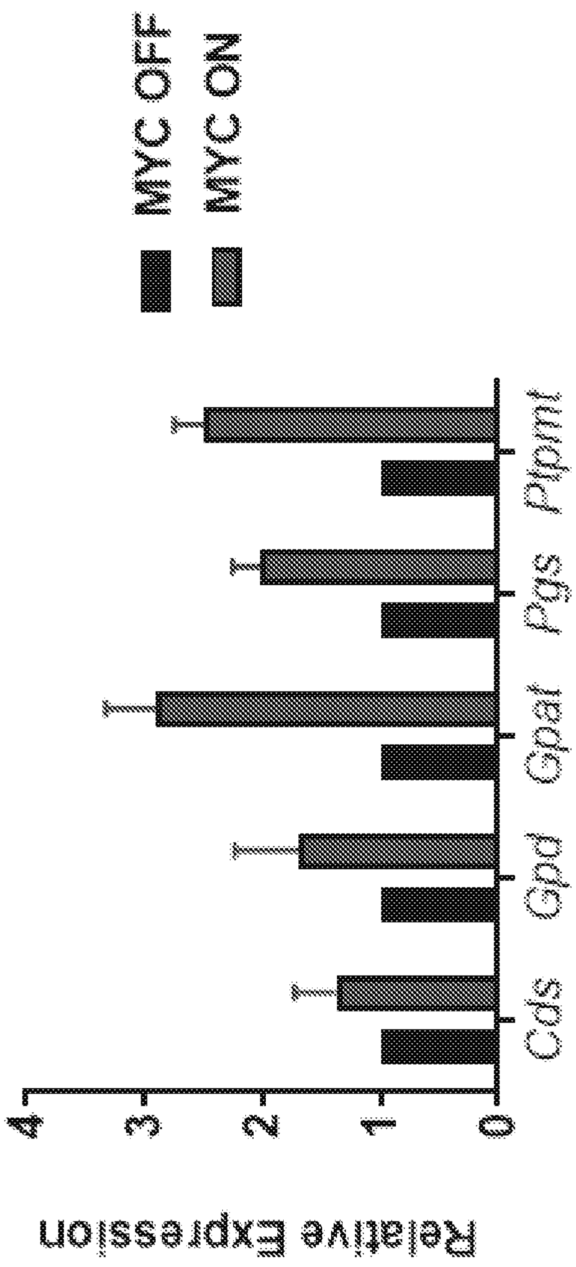
FIG. 3. MYC induces PG synthesis. Graph depicts RCC E28 PG synthesis pathway, illustrating mRNA expression of PG synthesis genes in RCC upon MYC activation.

As shown in FIGS. 1 and 3, MYC induces PG synthesis and regulates of PG synthesis genes, including GPAM or GPAT. A lipid signature of MYC-induced cancers is shown in FIG. 2.

Figure 4:
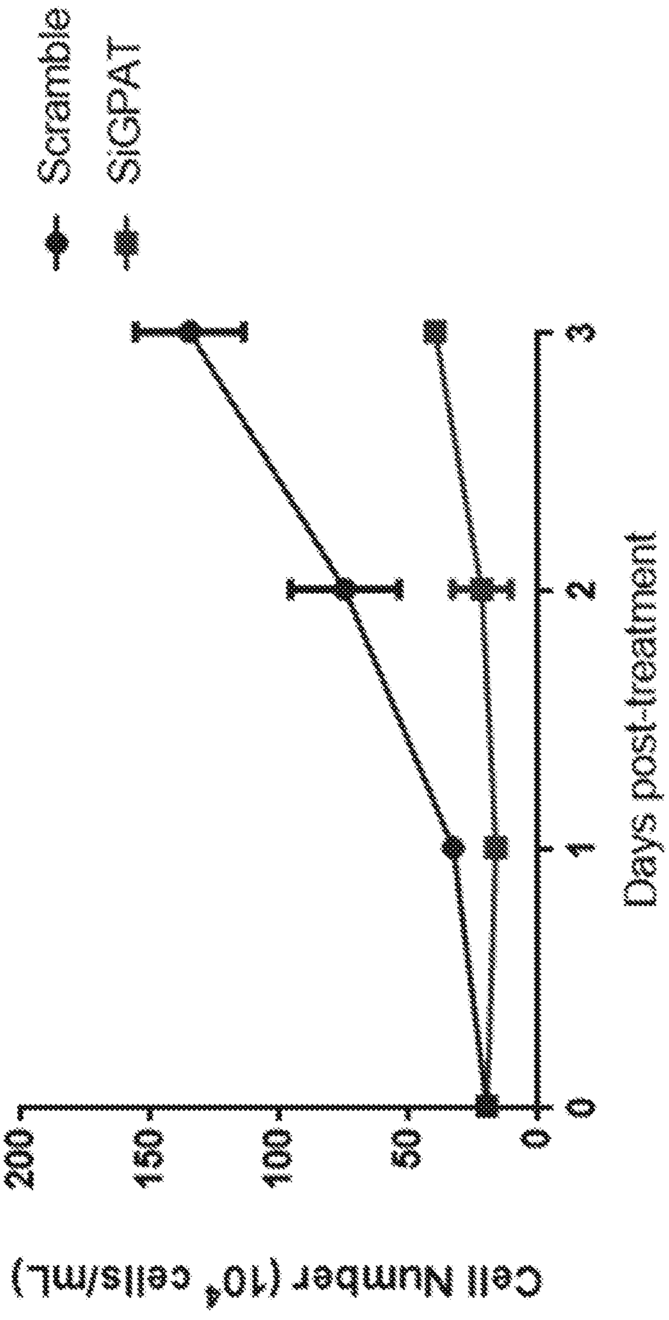
FIG. 4. siGPAT knockdown of GPAT in mouse-derived renal cell carcinoma line E28 suppresses cell proliferation. Statistical significance by t-test for MYC ON compared to control, *P<0.05, P<0.01, *P<0.001.
Figure 5:
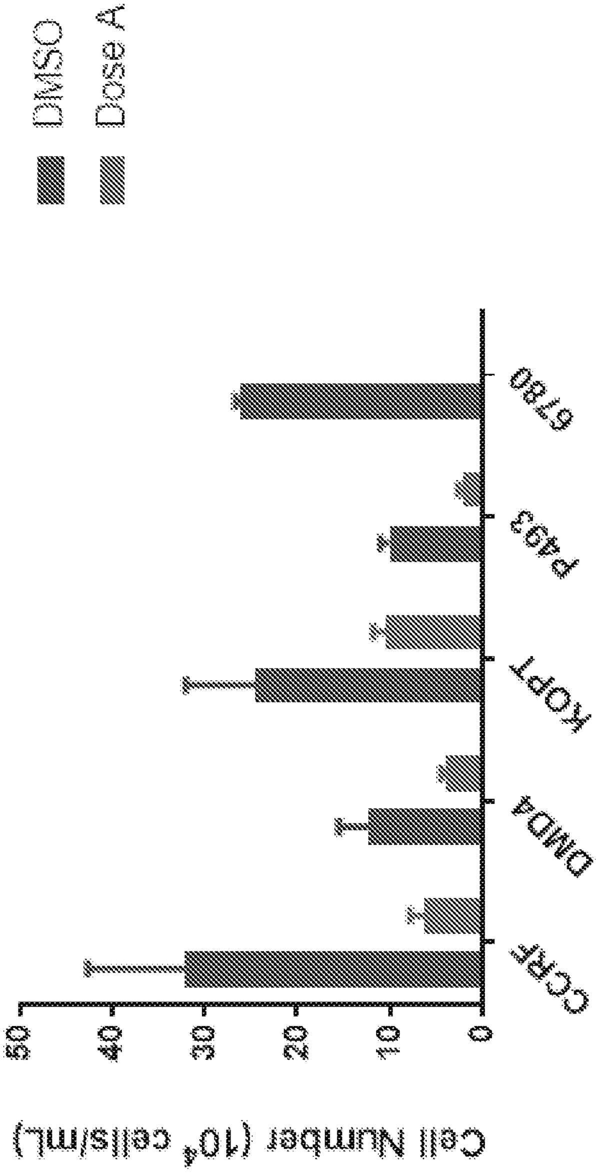
FIG. 5. GPAT inhibition suppresses proliferation of lymphoma lines. Shows FSG67 treatment (Dose A: 1-100 μM) for 24 hours in various human lymphoma lines suppresses cell proliferation.
Figure 6:
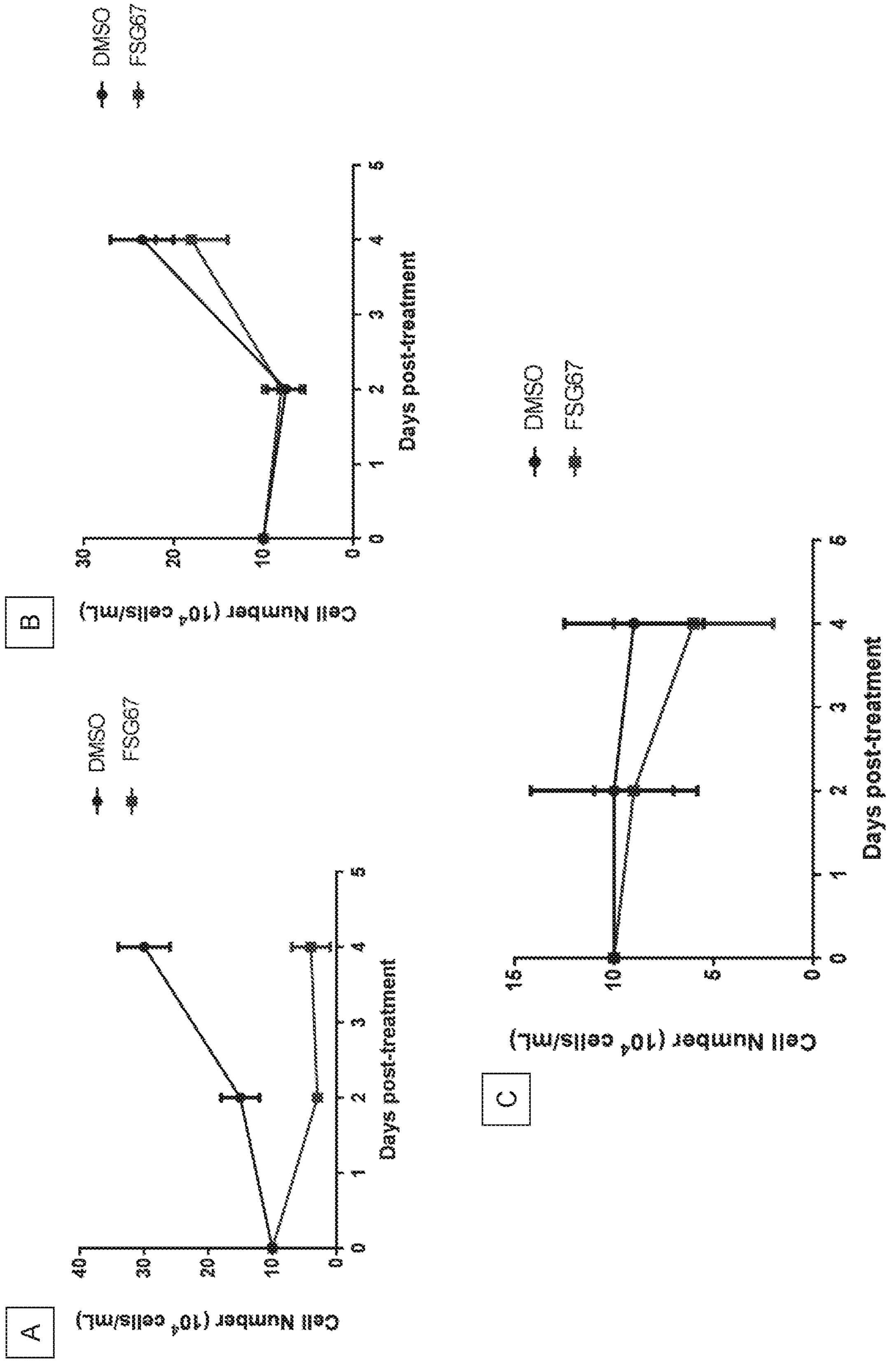
FIG. 6, panels A to C FSG67 treatment (1-100 μM) induced a therapeutic response in high MYC (no dox) (panel A) vs. low (panel B) or no MYC (panel C). MYC levels are controlled by doxycycline-off system in mouse-derived T-ALL line.
Figure 7:
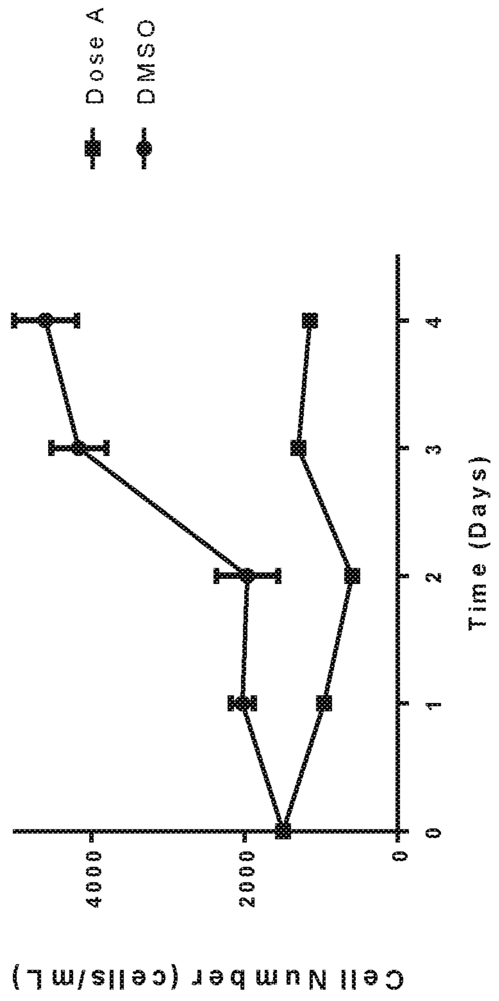
FIG. 7. FSG67 suppresses RCC E28 proliferation. Treatment with a GPAT inhibitor FSG67 (Dose A: 1-100 μM) induced a therapeutic response. Statistical significance by t-test for MYC ON compared to control, *P<0.05, P<0.01, *P<0.001.
Figure 8:
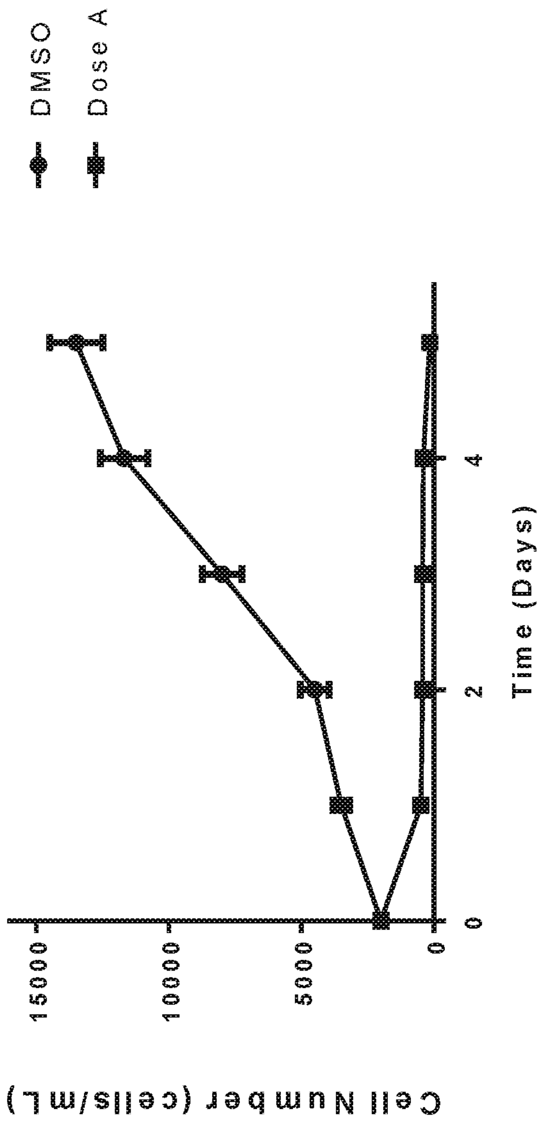
FIG. 8. FSG67 suppresses HCC EC4 proliferation. Treatment with a GPAT inhibitor FSG67 (Dose A: 1-100 μM) induced a therapeutic response. Statistical significance by t-test for MYC ON compared to control, *P<0.05, P<0.01, *P<0.001.

Inhibition of GPAT suppresses cancer cell proliferation (FIG. 4-FIG. 5). In vivo, FSG67 treatment induces therapeutic response in high MYC (no dox) vs. low or no MYC, shown in FIG. 6. FSGS67 suppresses RCC E28 proliferation (FIG. 7), or suppresses HCC EC4 proliferation (FIG. 8).

Figure 9:
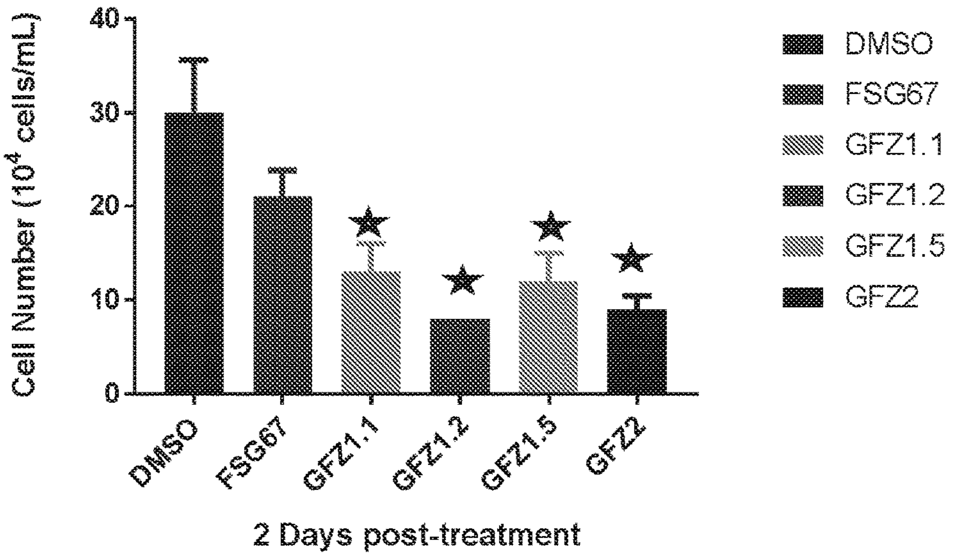
FIG. 9. Comparison of FSG67 and exemplary subject compounds in HCC EC4. Cell viability was measured two days post treatment with the respective GPAT inhibitors. There is significant difference in cell viability 2 days after treatment with FSG67 (1-100 μM dose) or any of GFZ1.1, GFZ1.2, GFZ1.5 or GFZ2 (1-100 μM dose). Statistical significance by t-test for MYC ON compared to control, *P<0.05, P<0.01, *P<0.001.
Figure 9:
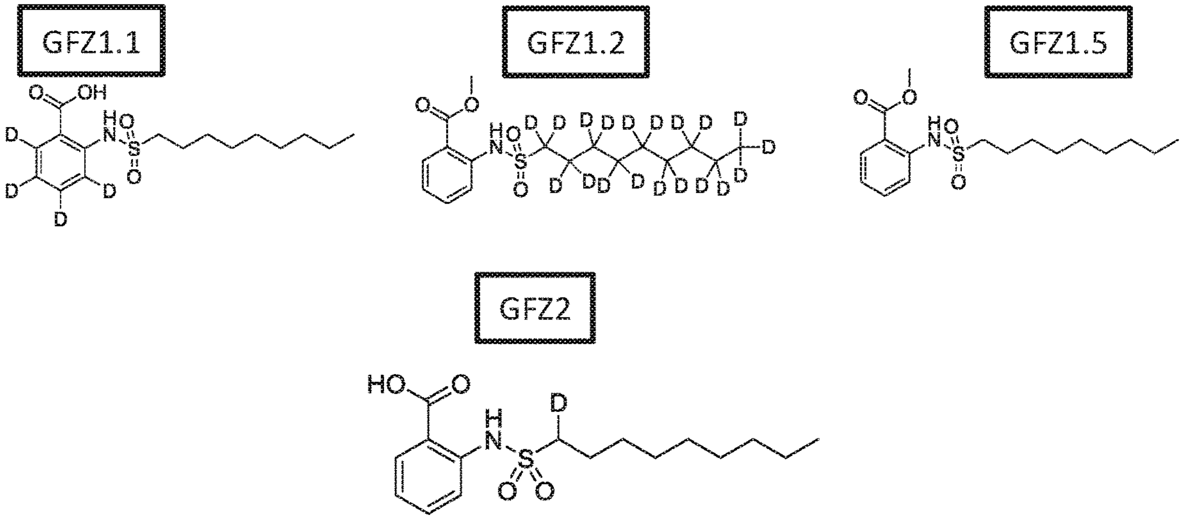
Figure 10:
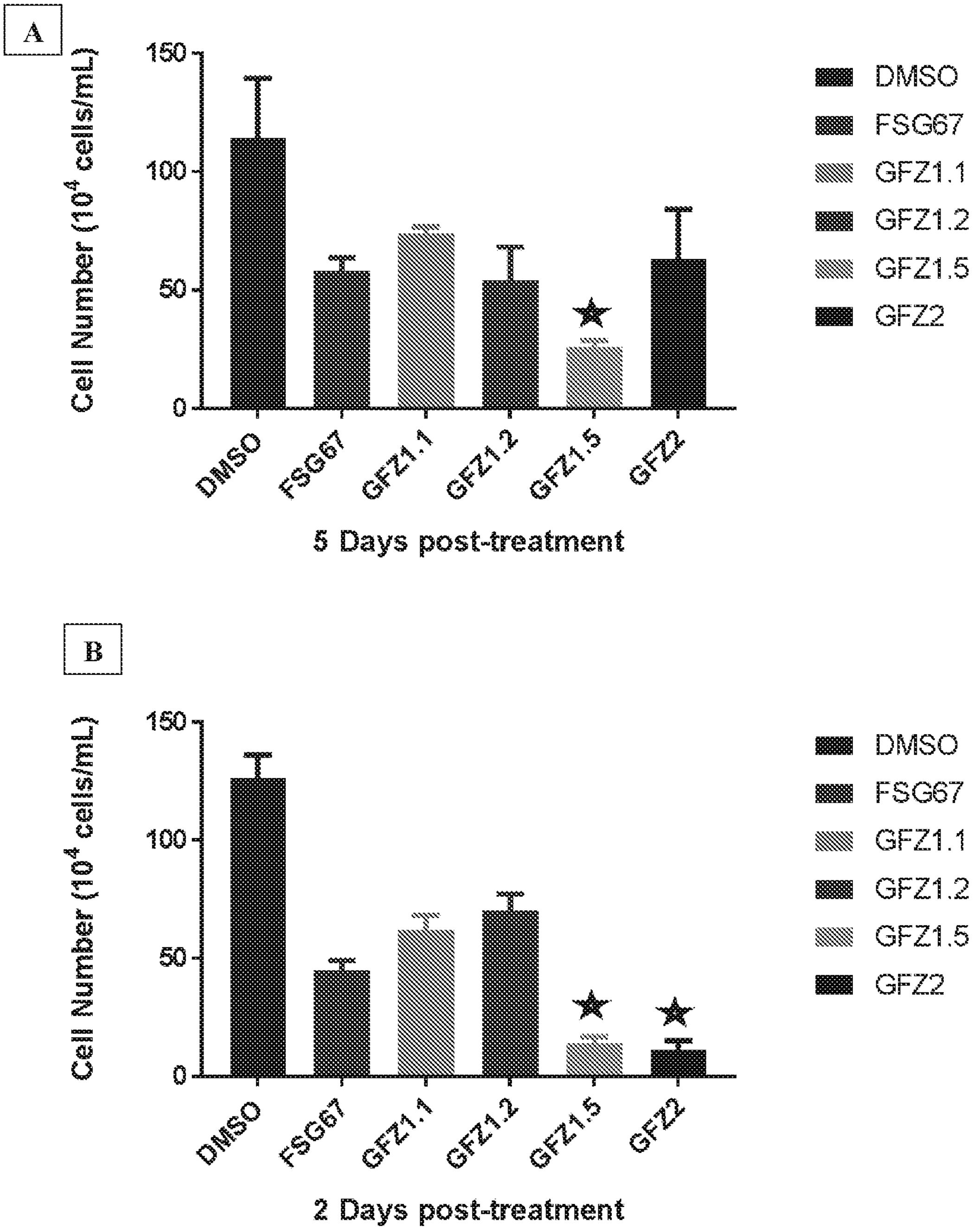
FIG. 10, panels A and B. Comparison of FSG67 and exemplary subject compounds in BCL 493 (panel A) and RCC E28 (panel B). Cell viability was measured five days (panel A) and two days (panel B) post treatment with the respective GPAT inhibitors. There is significant difference in cell viability in BCL 493 5 days after treatment with FSG67 (1-100 μM dose) or GFZ1.5 (1-100 μM dose). There is significant difference in cell viability in RCC E28 2 days after treatment with FSG67 (1-100 μM dose) or either of GFZ1.5 or GFZ2 (1-100 μM dose). Statistical significance by t-test for MYC ON compared to control, *P<0.05, P<0.01, *P<0.001.

FSG67 and exemplary compounds GFZ1.1, GFZ1.2, GFZ1.5 and GFZ2 (also referred to herein as compounds 3, 10, 11 and 6 respectively) were assayed for activity against HCC EC4 (FIG. 9), BCL P493 (FIG. 10, panel A) and RCC E28 (FIG. 10, panel B). In the assay for activity against the HCC EC4 line, significant difference in cell viability was observed after treatment with any of GFZ1.1, GFZ1.2, GFZ1.5 or GFZ2 (1-100 μM dose) as compared to FSG67 (See, e.g., FIG. 9). In the assay for activity against the BCL P493 line, significant difference in cell viability was observed after treatment with GFZ1.5 as compared to FSG67. In the assay for activity against the RC E28 line, significant difference in cell viability was observed after treatment with either of GFZ1.5 or GFZ2 as compared to FSG67.

Figure 11:
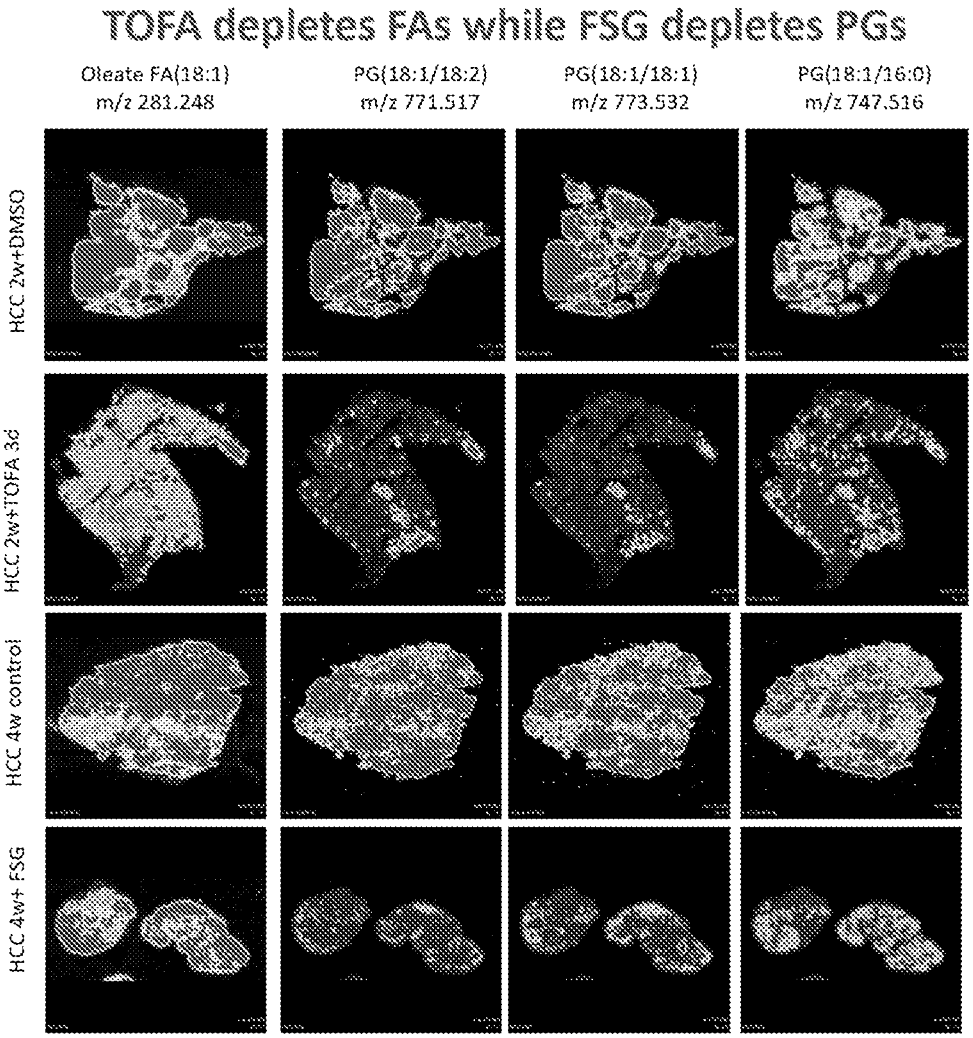
FIG. 11. TOFA depletes all fatty acids (first vs. second row), while FSG67 depletes only PGs (third vs. fourth row), while not perturbing levels of fatty acids that are upstream of GPAT (fourth row, first column—oleate).

Shown in FIG. 11, the administration of TOFA depletes all fatty acids (first vs. second row), while FSG67 depletes only PGs (third vs. fourth row), while not perturbing levels of fatty acids that are upstream of GPAT (fourth row, first column—oleate).

Figure 12:
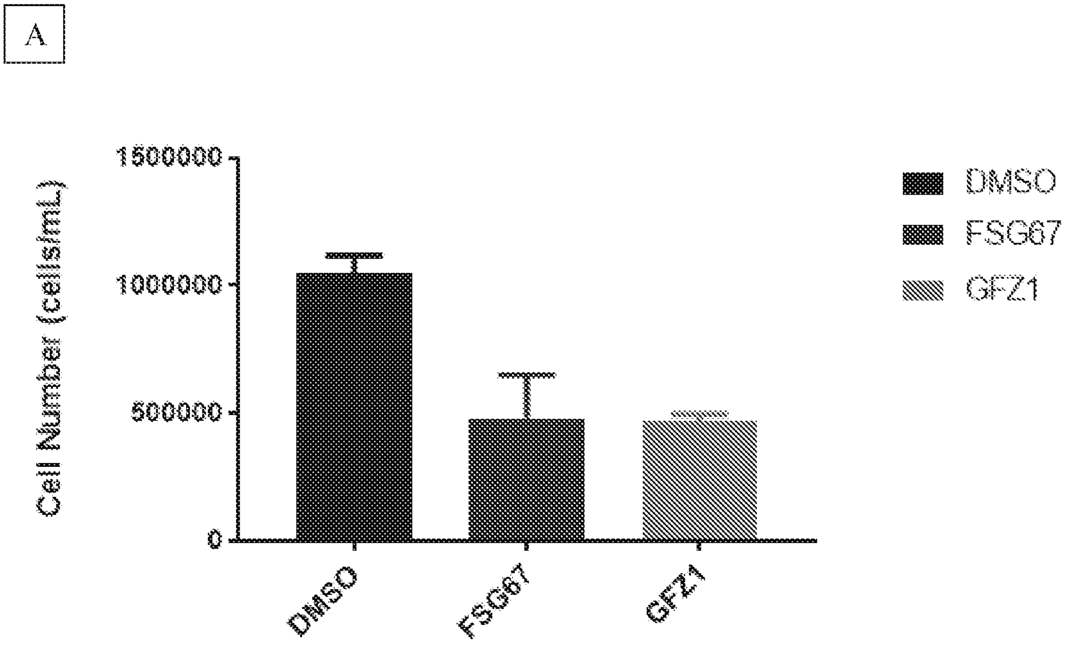
FIG. 12, panels A-D. Comparison of FSG67 and GFZ1.
Figure 12:
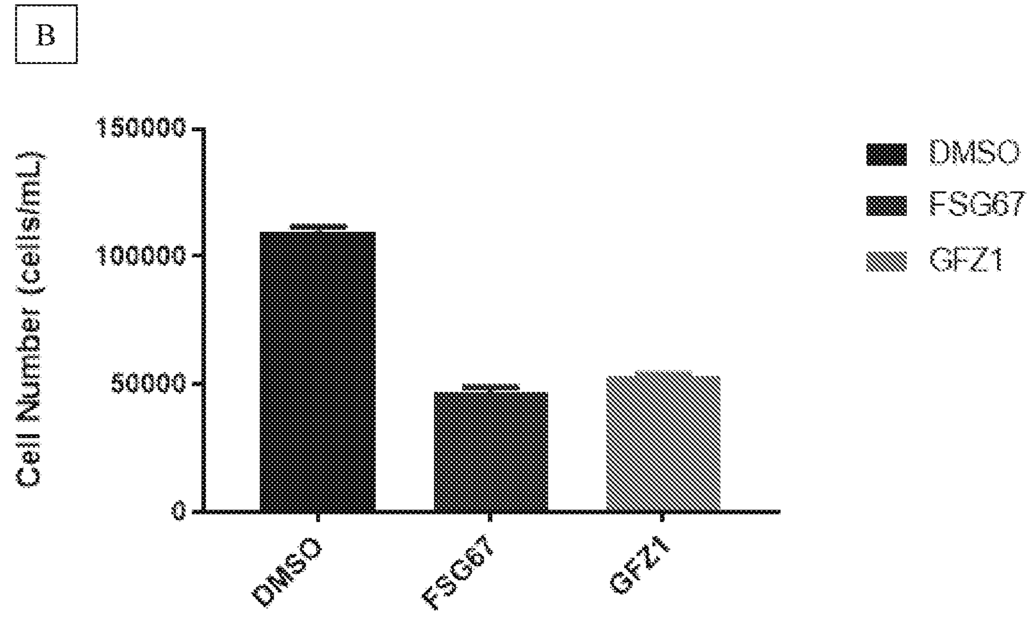

The deuterated compound GFZ1, is shown in FIG. 12D, and assayed for activity against HCC, RCC and lymphoma cell lines in FIG. 12 panel A-C. In human MYC-induced Burkitt's Lymphoma line P493, there is significant difference in cell viability 48 hours after treatment with GFZ1 (1-100 μM dose) vs FSG67 (1-100 μM dose).

Methods

DESI-MSI was used for generating two-dimensional chemical maps of 16 μm-thick tissue sections in order to assess the lipid profiles of tissue. The tissue samples were snap-frozen in liquid nitrogen and stored at −80° C. before processing. The frozen samples were cut into 16 μm sections at −21° C. using a cryomicrotome and thaw-mounted onto microscope slides. The slides were stored at −80° C. Prior to analysis, the slides were dried under a vacuum in a desiccator for approximately 20 minutes. A laboratory-built DESI-MSI source coupled to an LTQ-Orbitrap-XL mass spectrometer (Thermo Fisher Scientific) was utilized, and DESI-MSI was performed in the negative ion mode at m/z 90-1,000 with a spatial resolution of 200 μm (FIG. S1). The Orbitrap was used as the mass analyzer while set to 60,000 resolving power. Mouse tissue samples were imaged by this method using dimethylformamide and acetonitrile (1:1) as a solvent system at a flow rate of 0.5 μL/min. The N2 pressure was set to 175 psi. In DESI-MSI, charged solvents are sprayed onto the tissue, resulting in molecules, such as metabolites and lipids, to be dissolved and extracted from the tissue surface, then transferred into a mass spectrometer for measurement of the mass-to-charge (m/z) ratios. The software ImgGenerator (freeware, www.msimaging.net/)

was used for converting raw files into 2D images. Spatially accurate ion images were assembled using BioMap software (freeware, www.maldi-msi.org/). After DESI-MSI, the same tissue section was subjected to a standard H&E staining for histopathologic evaluation using light microscopy. DESI-MS ion images were compared with optical microscopy images of the same-tissue H&E-stained tissue sections for delineation of tumor foci. Tandem MS analyses were performed using both the Orbitrap and the linear ion trap for mass analysis to confirm lipid identity. The LipidMaps database (www.lipidmaps.org/) was also used to assist in lipid identification.

Nanoimmunoassay (NIA). NIA was performed using the Nanopro 1000 (Protein Simple) to detect protein levels in lysates generated from tissues. NIA is a highly sensitive capillary-based isoelectric focusing method that uses antibody detection to quantify protein isoforms as well as characterize post-translational protein modifications such as phosphorylation. The final protein concentration loaded into each capillary of the Nanopro 1000 was 0.1 μg/μL. All anti-mouse and anti-rabbit secondary antibodies, conjugated to horse radish peroxidase, were diluted 1:100. Chemiluminescence signal was recorded following the addition of luminol and peroxide detection reagents. Analysis of NIA data was performed in Compass software (Protein Simple).

Real-time PCR was performed in 384-well plates on the QuantStudio™ 12K Flex Real-Time PCR System. Amplicons were detected by using SYBR® Green I dye as fluorophore. Reactions were carried out in 20 μL volumes that contained 1 μL cDNA, 0.5 μM forward and reverse primers, and SYBR® Green PCR Master Mix (Applied Biosystems). Amplification cycle was set as follows: 50° C. for 2 minutes; 95° C. for 10 minutes; 40 cycles of 95° C. for 15 seconds, 60° C. for 1 minute, 72° C. for 30 seconds. Following the amplification stage, a melt curve was performed to identify any non-specific amplification. For each gene, a threshold cycle (Ct) number, which represents the number of cycles required to reach the threshold fluorescence, was determined. The Ct values were exported into Excel for statistical analysis. Ubiquitin (UBC) was used as a housekeeping (reference) gene. The 2-ΔΔCT method was used to determine relative mRNA expression levels.

Cell Counting. A volume of cells was removed from culture medium and mixed with an equal volume of 0.4% Trypan blue stain. Then, 10 μL were taken out and placed into a hemocytometer for cell counting. Viable cell counts were used as a measure of cell proliferation.

All RCC cell lines were maintained in Dulbecco's Modified Eagle Medium (DMEM) supplemented with 10% fetal bovine serum (FBS), 1% L-glutamine, 1% sodium pyruvate, 1% nonessential amino acids, and Antibiotic-Antimycotic. All lymphoma lines were maintained in RPMI 1640 medium supplemented with 10% FBS, 50 μM β-mercaptoethanol, and Antibiotic-Antimycotic. Trypsin-EDTA was used to passage adherent cells. All cell culture reagents were purchased from Gibco® (Thermo Fisher Scientific Inc.).

A Tet system was used to conditionally activate MYC, in the liver, kidney, lymphocyte, and lung tissue of transgenic mice. In this system, the gene encoding a tetracycline transactivating factor (tTA). In the absence of tetracycline, transcription of the oncogene is activated. Oncogene expression was activated in mice by removal of doxycycline (a stable analog of tetracycline) in the mice's drinking water. All animal studies were approved by the Stanford University Administrative Panel on Laboratory Animal Care (APLAC).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A GPAT inhibitor of one of formulae (IA), (IB), (IC):

(IA)

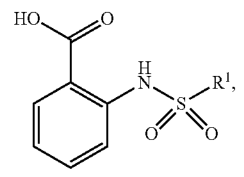

(IB)

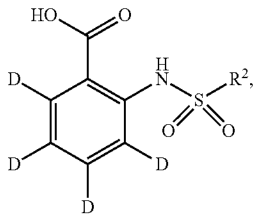

or (IC)

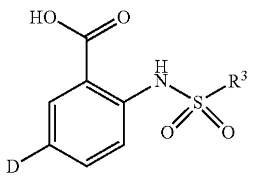

wherein:

$R^1$ is selected from deuterated alkyl and substituted deuterated alkyl;

$R^2$, and $R^3$ are each independently selected from alkyl, substituted alkyl, deuterated alkyl and substituted deuterated alkyl;

or a pharmaceutically acceptable salt or solvate thereof.

2. The GPAT inhibitor of claim 1, selected from the compounds:

(1)

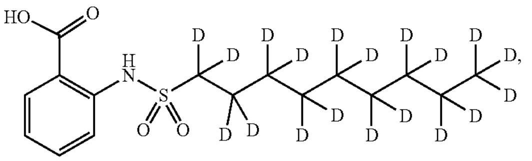

or (2)

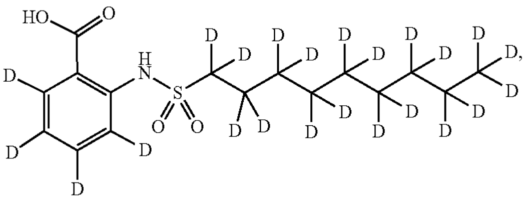

or (3)

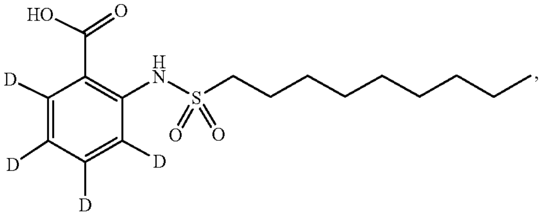

or (4)

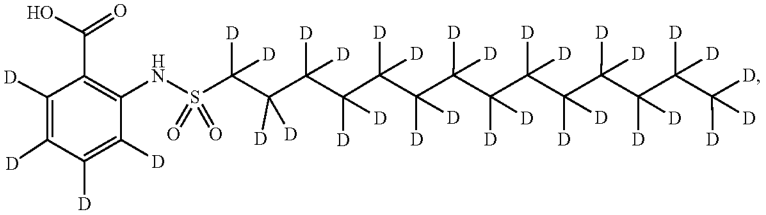

or (5)

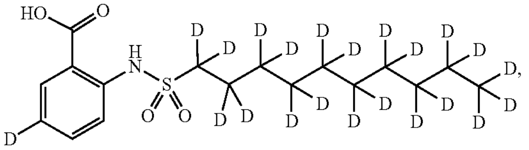

or (6)

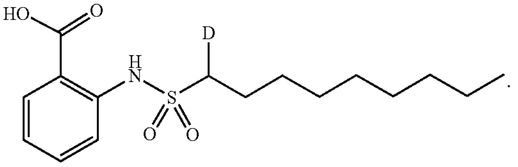

3. A pharmaceutical composition, comprising:

a GPAT inhibitor of claim 1; and a pharmaceutically acceptable excipient.

4. A method of treating a subject for cancer, the method comprising:

administering an effective dose of a GPAT inhibitor according to claim 1 for a period of time sufficient to inhibit growth of the cancer.

5. The method of claim 4, wherein the cancer is a MYC-dependent cancer.

6. The method of claim 4, wherein the cancer is selected from renal cell carcinoma, hepatocellular carcinoma, and lymphoma.

7. The method of claim 4, wherein the cancer is a hepatic cancer.

8. The method of claim 4, wherein the cancer is a lipogenesis-dependent neoplasm.

9. The method of claim 4, comprising:

comparing a lipogenesis profile obtained from a subject having a neoplasm with a reference lipogenesis profile to classify whether the neoplasm is lipogenesis-dependent; and administering to the subject an effective amount of a GPAT inhibitor of claim 1, when the neoplasm is classified as lipogenesis-dependent, to treat the subject for the lipogenesis-dependent neoplasm.

10. The method of claim 4, wherein the subject is a mammal.

11. The method of claim 10, wherein the mammal is a human.

12. A method of treating a metabolic syndrome related disease, the method comprising:

administering to a subject an effective dose of a GPAT inhibitor according to claim 1 for a period of time sufficient to reduce symptoms of the disease in the subject.

13. The method of claim 12, wherein the disease is selected from hyperlipidemia, metabolic syndrome, type 2 diabetes, fatty liver disease and obesity.

14. The method of claim 13, wherein the disease is obesity.

15. The method of claim 12, wherein the subject is a mammal.

16. The method of claim 15, wherein the mammal is a human.

* * * * *